United States Patent
Yokoyama et al.

(10) Patent No.: US 9,062,291 B2
(45) Date of Patent: Jun. 23, 2015

(54) TRANSGLUTAMINASE HAVING DISULFIDE BOND INTRODUCED THEREIN

(75) Inventors: Keiichi Yokoyama, Kawasaki (JP);
Mototaka Suzuki, Kawasaki (JP);
Tatsuki Kashiwagi, Kawasaki (JP);
Eiichiro Suzuki, Kawasaki (JP);
Masayo Date, Kawasaki (JP); Seiichi Taguchi, Sapporo (JP)

(73) Assignee: AJINOMOTO CO., INC., Tokyo (JP)

( * ) Notice: Subject to any disclaimer, the term of this patent is extended or adjusted under 35 U.S.C. 154(b) by 966 days.

(21) Appl. No.: 12/541,220

(22) Filed: Aug. 14, 2009

(65) Prior Publication Data
US 2010/0143970 A1    Jun. 10, 2010

Related U.S. Application Data

(63) Continuation of application No. PCT/JP2008/052470, filed on Feb. 14, 2008.

(30) Foreign Application Priority Data

Feb. 15, 2007   (JP) ................ 2007-034916

(51) Int. Cl.
*C12N 9/10*    (2006.01)

(52) U.S. Cl.
CPC ....... *C12N 9/1044* (2013.01); *C12Y 203/02013* (2013.01)

(58) Field of Classification Search
CPC ............ C12N 9/1044; C12Y 203/02013
See application file for complete search history.

(56) References Cited

U.S. PATENT DOCUMENTS

| | | | | |
|---|---|---|---|---|
| 4,990,452 | A | * | 2/1991 | Bryan et al. ............ 435/222 |
| 5,223,409 | A | * | 6/1993 | Ladner et al. ............ 506/1 |
| 7,252,972 | B2 | | 8/2007 | Kikuchi et al. |
| 7,312,058 | B2 | | 12/2007 | Kashiwagi et al. |
| 2004/0002144 | A1 | | 1/2004 | Kashiwagi et al. |
| 2006/0019367 | A1 | | 1/2006 | Umezawa et al. |
| 2007/0184525 | A1 | | 8/2007 | Date et al. |

FOREIGN PATENT DOCUMENTS

| | | |
|---|---|---|
| EP | 1 310 560 | 5/2003 |
| JP | 2002-253272 | 9/2002 |

OTHER PUBLICATIONS

Hazes, B., et al., 1988, "Model building of disulfide bonds in proteins with known three dimensional structure", Protein Engineering, vol. 2, No. 2, pp. 119-125.*

Clarke, J., et al., 1993, "Engineered disulfide bonds as probes of the folding pathway of barnase: Increasing the stability of proteins against the rate of denaturation", Biochemistry, vol. 32, No. 16, pp. 4322-4329.*

Shimaoka, M., et al., 2002, "Stabilizing the integrin alphaM inserted domain in alternative conformations with a range of engineered disulfide bonds", Proceedings of the National Academy of Sciences, USA, vol. 99, No. 26, pp. 16737-16741.*

(Continued)

*Primary Examiner* — Manjunath Rao
*Assistant Examiner* — William W Moore
(74) *Attorney, Agent, or Firm* — Shelly Guest Cermak; Cermak Nakajima & McGowan LLP

(57) ABSTRACT

A transglutaminase protein which is mutated to have improved heat resistance and/or pH stability. A mutation is introduced into WT transglutaminase at a cysteine residue capable of forming a disulfide bond (SS bond).

8 Claims, 4 Drawing Sheets

Heat resistance evaluation results 1

| | No treatment | 55°C | 60°C | 65°C | 68°C |
|---|---|---|---|---|---|
| 93/112 | 100 | 44.6 | 12.1 | 1.4 | 1.4 |
| 46/318 | 100 | 23.9 | 9.6 | 3.4 | 3.5 |
| 106/213 | 100 | 31.9 | 12.6 | 3.3 | 4.0 |
| 7/58 | 100 | 98.1 | 88.6 | 28.0 | 0.5 |
| Purified MTG (WT) | 100 | 83.6 | 38.3 | 0.1 | 0.1 |

(56) References Cited

OTHER PUBLICATIONS

Siadet, O. R., et al., 2006, "The effect of engineered disulfide bonds on the stability of Drosophila melanogaster acetylcholinesterase", BMC Biochemistry, vol. 7, pp. 1-12 of 12.*

Pellequer, J.-L., et al., 2006, "Multi-template approach to modeling engineered disulfide bonds", Proteins: Structure, Function, and Bioinformatics, vol. 65, pp. 192-202.*

Clarke, J., et al., "Engineered Disulfide Bonds as Probes of the Folding Pathway of Barnase: Increasing the Stability of Proteins against the Rate of Denaturation," Biochem. 1993;32:4322-4329.

KASHIWAGI, T., et al., "Crystal Structure of Microbial Transglutaminase from Streptoverticillium mobaraense," J. Biol. Chem. 2002;277(46):44252-44260.

Marx, C. K., et al., "Random mutagenesis of a recombinant microbial transglutaminase for the generation of thermostable and heat-sensitive variants," J. Biotechnol., doi: 10.1016/j.jbiotec.2008.06.005.

Matsumura, M., et al., "Substantial increase of protein stability by multiple disulphide bonds," Nature 1989;342(6247):291-293.

Perry, L. J., et al., "Disulfide Bond Engineered into T4 Lysozyme: Stabilization of the Protein Toward Thermal Inactivation," Science 1984;226(4674):555-557.

Ó'Fágáin, C., "Enzyme stabilization—recent experimental progress," Enzyme and Microbial Technology 2003;33:137-149.

Copy of Supplementary European Search Report for European Patent App. No. 08711306.4 (May 31, 2010).

Li, Y., et al., "Effect on thermostability and catalytic activity of introducing disulfide bonds into Aspergillus awamori glucoamylase," Protein Engineering 1998;11(8):661-667.

Copy of International Search Report for PCT Patent App. No. PCT/JP2008/052470 (May 13, 2009).

* cited by examiner

Heat resistance evaluation results 1

|  | No treatment | 55°C | 60°C | 65°C | 68°C |
|---|---|---|---|---|---|
| 93/112 | 100 | 44.6 | 12.1 | 1.4 | 1.4 |
| 46/318 | 100 | 23.9 | 9.6 | 3.4 | 3.5 |
| 106/213 | 100 | 31.9 | 12.6 | 3.3 | 4.0 |
| 7/58 | 100 | 98.1 | 88.6 | 28.0 | 0.5 |
| Purified MTG (WT) | 100 | 83.6 | 38.3 | 0.1 | 0.1 |

Heat resistance evaluation results 2

FIG. 3

| pH  | 3    | 4    | 6   | 9    | 10    |
|-----|------|------|-----|------|-------|
| MTG | 60.1 | 96.7 | 100 | 99.5 | 101.2 |
| 7/58| 88.7 | 99.4 | 100 | 99.8 | 99.3  |

FIG. 4

```
s.cinnamoneus   1:--SDDRETPPAEPLDRMPEAYRAYGGRAFTVVNNYIRKWQQYYSHRDGKKQMTEEQREKLSYGCVGVTWVNSGFYPTNR  78
s.fradiae       1:ALVDDRETPPAEPLDRMPDAYRAYGGRAFTVVNNYIRKWQQVYSHRDGKKQQMTEEQRENLSYGCVGVTWVNSGFYPTNK  80
s.ladakanum     1:--DSDERVTPPAEPLDRMPDEYRPSYGRAETVVNNYIRKWQQVYSHRDGRKQQMTEEQREWLSYGCVGVTWVASGQYPTNR  79
s.lydicus       1:--RADERVTPPAEPLNRMPDAYRAYGGRAFTVVNNYIRKWQQVTAHRDGIQQQMTEEQREKLSYGCVGITWVNSGPYPTNK  79
s.mobaraensis   1:--DSDDRVTPPAEPLDRMPDYRESYGRAETVVNNYIRKWQQVYSHRDGRKQQMTEEQREWLSYGCVGVTWVNSGQYPTNR  79
s.platensis     1:DAVDDRVTPPAEPLNRMPDAYRAYGGRAFTVVNNYIRKWCQVYSQRGNPDQMTEEQREQLSYGCVTWVNTGFYPTNK     80
                                                                                                * s.cinnamoneus  79:LAEFASFDENKYKNDLKWTSPRQDETRAFPEGRIAKGSFDEGKGFYKARDVASVMRKALENAHDEGTYIRNLKTELTNWND 158
s.fradiae      81:LAEFASFDENKYKNDLKWTSPRPNETRAEFEGRIAKGSFDEGKGFYKARDVASVMRKALENAPDEGTYLKRNLKTDLNKWND 160
s.ladakanum    80:LAEFAFEDECKYRNELFQWGRPRSGETFALFEGRVAKDSFDEAKGFQRARDVASVMNKALENAHDEGAYLDNLKKELAWGND 159
s.lydicus      80:LAEFAFFDENKYKSDENSRFRPNETQAEFEGRIVKDSFDEGKGFYRARDVASVMNKALESAHDEGTYIDMLKTELAHAND   159
s.mobaraensis  80:LAEFASFDEDRFKNELKNCRPRSGETRAEFEGRVAKESFDEEKGFKRAREVASVNRIRALSMAHDESAYLDNLKKELANERD 159
s.platensis    81:LAEFAFFDENKYKMDLENSKRPNETQAEFEGRIAKDSFDEGKGFKRAREVASVMNKALDNAHDEGTYIGHLKKELAWGND   160
                                                                                                * s.cinnamoneus 159:ALLREDERSNEYSALRNTPSFKGRDGGNYDPSKMGAVIYSKMEWSGQDPGYVTDMSKDRS 238
s.fradiae     161:ALLHEDSRSNEYSALRNTPSFKGRDGGNYDESKMKAVIYSKMEWSGQDQDRGSADKRKYGDAEAFREDQGTGLVLDMSKDRN 240
s.ladakanum   160:ALRNEDARSPFYSALRNTPSFKDRANGGNADPSRMKAVVYSRMKAVIYSKMEWSGQDRSGSSDKRKYGDPEAFREDRGTGLVDMSRDRN 239
s.lydicus     160:ALRYEDGRSNFYSALRNTPSFKCRDGGRNYDPSKMKAVVYSKMEWSGQDQRGSSDKRKYGDPDAFREDGSTGLVDMSKDRN 239
s.mobaraensis 160:ALRNEDARSPFYSALRNTPSFKEKERNGSRHDPSRMGAVIYSKMEWSGQDRSSSADKRKYGDPDATRAPSTGLVDMSRDRN 239
s.platensis   151:ALLXEDSRSSYYSALRNTPSFKERDGGNYDPSKMAVVVYSKMEWSGQDQRGSSEKGKYGDPDAFRPGQGTGLVDMSRDRN   240
                     *  *                                                                            * s.cinnamoneus 239:IPRSPAKPGEGRVNTDYGWTGRQVEADADKTTWTHGDRHYHAPNSDLGEMHVHESKFRKWSAGYADFDRGAVITFIPKSW 318
s.fradiae     241:IPRSPAKPGEGWVNTDYGWFGAQTGADADETTWTRGDRYHAPNSGLGEMHVHESKFRKWSAGYADFDRGYVITFIPKSW   320
s.ladakanum   240:IPRSPTSPGESFVNEDYGWFGAQTEADTEADADKTVWTHGNHYHAPNGSLGAMHVYESKERNWSDGYSDFDRGAYVITFVPKSW 319
s.lydicus     240:IPRSPRAQPGESWVNEDYGWFGRAQTESDADKTIWTHANHYHAEMGGLGEMNVYESKERNWSAGYADFDRGTYVITFIPKSW   319
s.mobaraensis 240:IPRSPTSPGEGFVNFDYGWFGAQTEADADKTVWTHGNHYHRENGSLGAMHVYESGYSDFDKGAYVITFIPKSW           319
s.platensis   241:IPRSPAKPGESWYNFDYGWFGA.QAEARADADKTVWTHPNHVHALPGGWKPMAVYSSKERNWSAGYADFDRGAVITFIPKSW 320 s.cinnamoneus 319:NTRPAKVEGGWP 330
s.fradiae     321:NTAPDKVEQGWP 332
s.ladakanum   320:NTAPDKVTQGWP 331
s.lydicus     320:NTAPAEVKQGWS 331
s.mobaraensis 320:NTAPDKVKQGWP 331
s.platensis   321:NTAPREVKQGWP 332
                  ****  * ***
```

FIG. 5

Heat resistance evaluation results 3

|  | No treatment | 60°C |
|---|---|---|
| 140/190 | 100 | 32.7 |
| 160/228 | 100 | 48.0 |
| Purified MTG (WT) | 100 | 38.2 |

FIG. 6

Heat resistance evaluation results 4

|  | No treatment | 60°C |
|---|---|---|
| 2/282 | 100 | 37.0 |
| 2/283 | 100 | 71.4 |
| 3/283 | 100 | 98.0 |
| Purified MTG (WT) | 100 | 31.5 |

FIG. 7

|  | pH3 | pH6 | pH12 |
|---|---|---|---|
| Purified MTG (WT) | 40.4 | 100 | 33.9 |
| 7/58 | 69.8 | 100 | 34.2 |
| 3/283 | 80.6 | 100 | 79.2 |
| 2/282 | 58.0 | 100 | 28.2 |
| 2/283 | 58.9 | 100 | 36.0 |

SEQUENCE LISTING

```
<160> NUMBER OF SEQ ID NOS: 16

<210> SEQ ID NO 1
<211> LENGTH: 993
<212> TYPE: DNA
<213> ORGANISM: Streptomyces mobaraensis
<220> FEATURE:
<221> NAME/KEY: CDS
<222> LOCATION: (1)..(993)

<400> SEQUENCE: 1 gac tcc gac gac agg gtc acc cct ccc gcc gag ccg ctc gac agg atg      48
Asp Ser Asp Asp Arg Val Thr Pro Pro Ala Glu Pro Leu Asp Arg Met
1               5                   10                  15 ccc gac ccg tac cgt ccc tcg tac ggc agg gcc gag acg gtc gtc aac      96
Pro Asp Pro Tyr Arg Pro Ser Tyr Gly Arg Ala Glu Thr Val Val Asn
            20                  25                  30 aac tac ata cgc aag tgg cag cag gtc tac agc cac cgc gac ggc agg     144
Asn Tyr Ile Arg Lys Trp Gln Gln Val Tyr Ser His Arg Asp Gly Arg
        35                  40                  45
```

```
aag cag cag atg acc gag gag cag cgg gag tgg ctg tcc tac ggc tgc       192
Lys Gln Gln Met Thr Glu Glu Gln Arg Glu Trp Leu Ser Tyr Gly Cys
 50                  55                  60 gtc ggt gtc acc tgg gtc aat tcg ggt cag tac ccg acg aac aga ctg       240
Val Gly Val Thr Trp Val Asn Ser Gly Gln Tyr Pro Thr Asn Arg Leu
 65                  70                  75                  80 gcc ttc gcg tcc ttc gac gag gac agg ttc aag aac gag ctg aag aac       288
Ala Phe Ala Ser Phe Asp Glu Asp Arg Phe Lys Asn Glu Leu Lys Asn
                 85                  90                  95 ggc agg ccc cgg tcc ggc gag acg cgg gcg gag ttc gag ggc cgc gtc       336
Gly Arg Pro Arg Ser Gly Glu Thr Arg Ala Glu Phe Glu Gly Arg Val
            100                 105                 110 gcg aag gag agc ttc gac gag gag aag ggc ttc cag cgg gcg cgt gag       384
Ala Lys Glu Ser Phe Asp Glu Glu Lys Gly Phe Gln Arg Ala Arg Glu
        115                 120                 125 gtg gcg tcc gtc atg aac agg gcc ctg gag aac gcc cac gac gag agc       432
Val Ala Ser Val Met Asn Arg Ala Leu Glu Asn Ala His Asp Glu Ser
    130                 135                 140 gct tac ctc gac aac ctc aag aag gaa ctg gcg aac ggc aac gac gcc       480
Ala Tyr Leu Asp Asn Leu Lys Lys Glu Leu Ala Asn Gly Asn Asp Ala
145                 150                 155                 160 ctg cgc aac gag gac gcc cgt tcc ccg ttc tac tcg gcg ctg cgg aac       528
Leu Arg Asn Glu Asp Ala Arg Ser Pro Phe Tyr Ser Ala Leu Arg Asn
                165                 170                 175 acg ccg tcc ttc aag gag cgg aac gga ggc aat cac gac ccg tcc agg       576
Thr Pro Ser Phe Lys Glu Arg Asn Gly Gly Asn His Asp Pro Ser Arg
            180                 185                 190 atg aag gcc gtc atc tac tcg aag cac ttc tgg agc ggc cag gac cgg       624
Met Lys Ala Val Ile Tyr Ser Lys His Phe Trp Ser Gly Gln Asp Arg
        195                 200                 205 tcg agt tcg gcc gac aag agg aag tac ggc gac ccg gac gcc ttc cgc       672
Ser Ser Ser Ala Asp Lys Arg Lys Tyr Gly Asp Pro Asp Ala Phe Arg
    210                 215                 220 ccc gcc ccg ggc acc ggc ctg gtc gac atg tcg agg gac agg aac att       720
Pro Ala Pro Gly Thr Gly Leu Val Asp Met Ser Arg Asp Arg Asn Ile
225                 230                 235                 240 ccg cgc agc ccc acc agc ccc ggt gag gga ttc gtc aat ttc gac tac       768
Pro Arg Ser Pro Thr Ser Pro Gly Glu Gly Phe Val Asn Phe Asp Tyr
                245                 250                 255 ggc tgg ttc ggc gcc cag acg gaa gcg gac gcc gac aag acc gtc tgg       816
Gly Trp Phe Gly Ala Gln Thr Glu Ala Asp Ala Asp Lys Thr Val Trp
            260                 265                 270 acc cac gga aat cac tat cac gcg ccc aat ggc agc ctg ggt gcc atg       864
Thr His Gly Asn His Tyr His Ala Pro Asn Gly Ser Leu Gly Ala Met
        275                 280                 285 cat gtc tac gag agc aag ttc cgc aac tgg tcc gag ggt tac tcg gac       912
His Val Tyr Glu Ser Lys Phe Arg Asn Trp Ser Glu Gly Tyr Ser Asp
    290                 295                 300 ttc gac cgc gga gcc tat gtg atc acc ttc atc ccc aag agc tgg aac       960
Phe Asp Arg Gly Ala Tyr Val Ile Thr Phe Ile Pro Lys Ser Trp Asn
305                 310                 315                 320 acc gcc ccc gac aag gta aag cag ggc tgg ccg                           993
Thr Ala Pro Asp Lys Val Lys Gln Gly Trp Pro
                325                 330
```

<210> SEQ ID NO 2
<211> LENGTH: 331
<212> TYPE: PRT
<213> ORGANISM: Streptomyces mobaraensis

<400> SEQUENCE: 2

```
Asp Ser Asp Asp Arg Val Thr Pro Ala Glu Pro Leu Asp Arg Met
1               5                   10                  15

Pro Asp Pro Tyr Arg Pro Ser Tyr Gly Arg Ala Glu Thr Val Val Asn
                20                  25                  30

Asn Tyr Ile Arg Lys Trp Gln Gln Val Tyr Ser His Arg Asp Gly Arg
            35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65              70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330

<210> SEQ ID NO 3
<211> LENGTH: 990
<212> TYPE: DNA
<213> ORGANISM: Streptomyces cinnamoneus
<220> FEATURE:
<221> NAME/KEY: CDS
<222> LOCATION: (1)..(990)

<400> SEQUENCE: 3 tcc gat gac cgg gaa act cct ccc gcc gag ccg ctc gac agg atg cct    48
Ser Asp Asp Arg Glu Thr Pro Pro Ala Glu Pro Leu Asp Arg Met Pro
1               5                   10                  15
```

```
gag gcg tac cgg gcc tac gga ggc agg gcc act acg gtc gtc aac aac      96
Glu Ala Tyr Arg Ala Tyr Gly Gly Arg Ala Thr Thr Val Val Asn Asn
             20                  25                  30 tac ata cgc aag tgg cag cag gtc tac agt cac cgc gac gga aag aaa     144
Tyr Ile Arg Lys Trp Gln Gln Val Tyr Ser His Arg Asp Gly Lys Lys
         35                  40                  45 cag caa atg acc gaa gag cag cga gaa aag ctg tcc tac ggt tgc gtt     192
Gln Gln Met Thr Glu Glu Gln Arg Glu Lys Leu Ser Tyr Gly Cys Val
     50                  55                  60 ggc gtc acc tgg gtc aac tcg ggc ccc tac ccg acg aac aga ttg gcg     240
Gly Val Thr Trp Val Asn Ser Gly Pro Tyr Pro Thr Asn Arg Leu Ala
 65                  70                  75                  80 ttc gcg tcc ttc gac gag aac aag tac aag aac gac ctg aag aac acc     288
Phe Ala Ser Phe Asp Glu Asn Lys Tyr Lys Asn Asp Leu Lys Asn Thr
                 85                  90                  95 agc ccc cga ccc gat gaa acg cgg gcg gag ttc gag ggt cgc atc gcc     336
Ser Pro Arg Pro Asp Glu Thr Arg Ala Glu Phe Glu Gly Arg Ile Ala
            100                 105                 110 aag ggc agt ttc gac gag ggg aag ggt ttc aag cgg gcg cgt gat gtg     384
Lys Gly Ser Phe Asp Glu Gly Lys Gly Phe Lys Arg Ala Arg Asp Val
        115                 120                 125 gcg tcc gtc atg aac aag gcc ctg gaa aat gcc cac gac gag ggg act     432
Ala Ser Val Met Asn Lys Ala Leu Glu Asn Ala His Asp Glu Gly Thr
130                 135                 140 tac atc aac aac ctc aag acg gag ctc acg aac aac aat gac gct ctg     480
Tyr Ile Asn Asn Leu Lys Thr Glu Leu Thr Asn Asn Asn Asp Ala Leu
145                 150                 155                 160 ctc cgc gag gac agc cgc tcg aac ttc tac tcg gcg ctg agg aac aca     528
Leu Arg Glu Asp Ser Arg Ser Asn Phe Tyr Ser Ala Leu Arg Asn Thr
                165                 170                 175 ccg tcc ttc aag gaa agg gac ggc ggc aac tac gac ccg tcc aag atg     576
Pro Ser Phe Lys Glu Arg Asp Gly Gly Asn Tyr Asp Pro Ser Lys Met
            180                 185                 190 aag gcg gtg atc tac tcg aag cac ttc tgg agc ggg cag gac cag cgg     624
Lys Ala Val Ile Tyr Ser Lys His Phe Trp Ser Gly Gln Asp Gln Arg
        195                 200                 205 ggc tcc tcc gac aag agg aag tac ggc gac ccg gaa gcc ttc cgc ccc     672
Gly Ser Ser Asp Lys Arg Lys Tyr Gly Asp Pro Glu Ala Phe Arg Pro
210                 215                 220 gac cag ggt acc ggc ctg gtc gac atg tcg aag gac aga agc att ccg     720
Asp Gln Gly Thr Gly Leu Val Asp Met Ser Lys Asp Arg Ser Ile Pro
225                 230                 235                 240 cgc agt ccg gcc aag ccc ggc gaa ggt tgg gtc aat ttc gac tac ggt     768
Arg Ser Pro Ala Lys Pro Gly Glu Gly Trp Val Asn Phe Asp Tyr Gly
                245                 250                 255 tgg ttc ggg gct caa aca gaa gcg gat gcc gac aaa acc aca tgg acc     816
Trp Phe Gly Ala Gln Thr Glu Ala Asp Ala Asp Lys Thr Thr Trp Thr
            260                 265                 270 cac ggc gac cac tac cac gcg ccc aat agc gac ctg ggc ccc atg cac     864
His Gly Asp His Tyr His Ala Pro Asn Ser Asp Leu Gly Pro Met His
        275                 280                 285 gta cac gag agc aag ttc cgg aag tgg tct gcc ggg tac gcg gac ttc     912
Val His Glu Ser Lys Phe Arg Lys Trp Ser Ala Gly Tyr Ala Asp Phe
290                 295                 300 gac cgc gga gcc tac gtg atc acg ttc ata ccc aag agc tgg aac acc     960
Asp Arg Gly Ala Tyr Val Ile Thr Phe Ile Pro Lys Ser Trp Asn Thr
305                 310                 315                 320 gcc ccc gcc aag gtg gag caa ggc tgg ccg                             990
Ala Pro Ala Lys Val Glu Gln Gly Trp Pro
                325                 330
```

-continued

<210> SEQ ID NO 4
<211> LENGTH: 330
<212> TYPE: PRT
<213> ORGANISM: Streptomyces cinnamoneus

<400> SEQUENCE: 4

Ser Asp Asp Arg Glu Thr Pro Pro Ala Glu Pro Leu Asp Arg Met Pro
1               5                   10                  15

Glu Ala Tyr Arg Ala Tyr Gly Gly Arg Ala Thr Thr Val Val Asn Asn
            20                  25                  30

Tyr Ile Arg Lys Trp Gln Gln Val Tyr Ser His Arg Asp Gly Lys Lys
        35                  40                  45

Gln Gln Met Thr Glu Glu Gln Arg Glu Lys Leu Ser Tyr Gly Cys Val
    50                  55                  60

Gly Val Thr Trp Val Asn Ser Gly Pro Tyr Pro Thr Asn Arg Leu Ala
65                  70                  75                  80

Phe Ala Ser Phe Asp Glu Asn Lys Tyr Lys Asn Asp Leu Lys Asn Thr
                85                  90                  95

Ser Pro Arg Pro Asp Glu Thr Arg Ala Glu Phe Glu Gly Arg Ile Ala
            100                 105                 110

Lys Gly Ser Phe Asp Glu Gly Lys Gly Phe Lys Arg Ala Arg Asp Val
        115                 120                 125

Ala Ser Val Met Asn Lys Ala Leu Glu Asn Ala His Asp Glu Gly Thr
    130                 135                 140

Tyr Ile Asn Asn Leu Lys Thr Glu Leu Thr Asn Asn Asn Asp Ala Leu
145                 150                 155                 160

Leu Arg Glu Asp Ser Arg Ser Asn Phe Tyr Ser Ala Leu Arg Asn Thr
                165                 170                 175

Pro Ser Phe Lys Glu Arg Asp Gly Gly Asn Tyr Asp Pro Ser Lys Met
            180                 185                 190

Lys Ala Val Ile Tyr Ser Lys His Phe Trp Ser Gly Gln Asp Gln Arg
        195                 200                 205

Gly Ser Ser Asp Lys Arg Lys Tyr Gly Asp Pro Glu Ala Phe Arg Pro
    210                 215                 220

Asp Gln Gly Thr Gly Leu Val Asp Met Ser Lys Asp Arg Ser Ile Pro
225                 230                 235                 240

Arg Ser Pro Ala Lys Pro Gly Glu Gly Trp Val Asn Phe Asp Tyr Gly
                245                 250                 255

Trp Phe Gly Ala Gln Thr Glu Ala Asp Ala Asp Lys Thr Thr Trp Thr
            260                 265                 270

His Gly Asp His Tyr His Ala Pro Asn Ser Asp Leu Gly Pro Met His
        275                 280                 285

Val His Glu Ser Lys Phe Arg Lys Trp Ser Ala Gly Tyr Ala Asp Phe
    290                 295                 300

Asp Arg Gly Ala Tyr Val Ile Thr Phe Ile Pro Lys Ser Trp Asn Thr
305                 310                 315                 320

Ala Pro Ala Lys Val Glu Gln Gly Trp Pro
                325                 330

<210> SEQ ID NO 5
<211> LENGTH: 996
<212> TYPE: DNA
<213> ORGANISM: Streptomyces fradiae
<220> FEATURE:
<221> NAME/KEY: CDS

<222> LOCATION: (1)..(996)

<400> SEQUENCE: 5

| | | | | | | | | | | | | | | | | |
|---|---|---|---|---|---|---|---|---|---|---|---|---|---|---|---|---|
| gcc | ctg | gtc | gac | gac | agg | gaa | acc | cct | ccc | gcc | gag | ccg | ctc | gac | agg | 48 |
| Ala | Leu | Val | Asp | Asp | Arg | Glu | Thr | Pro | Pro | Ala | Glu | Pro | Leu | Asp | Arg | |
| 1 | | | | 5 | | | | | 10 | | | | | 15 | | |

| atg | ccc | gac | gcg | tac | cgg | gcc | tac | gga | ggc | aga | gcc | act | acg | gtc | gtc | 96 |
|---|---|---|---|---|---|---|---|---|---|---|---|---|---|---|---|---|
| Met | Pro | Asp | Ala | Tyr | Arg | Ala | Tyr | Gly | Gly | Arg | Ala | Thr | Thr | Val | Val | |
| | | | 20 | | | | | 25 | | | | | 30 | | | |

| aac | aac | tac | ata | cgc | aag | tgg | cag | cag | gtc | tac | agt | cag | cgc | gac | ggc | 144 |
|---|---|---|---|---|---|---|---|---|---|---|---|---|---|---|---|---|
| Asn | Asn | Tyr | Ile | Arg | Lys | Trp | Gln | Gln | Val | Tyr | Ser | Gln | Arg | Asp | Gly | |
| | | 35 | | | | | 40 | | | | | 45 | | | | |

| aag | aag | cag | caa | atg | acc | gaa | gag | cag | cga | gag | aac | ctg | tcc | tac | ggt | 192 |
|---|---|---|---|---|---|---|---|---|---|---|---|---|---|---|---|---|
| Lys | Lys | Gln | Gln | Met | Thr | Glu | Glu | Gln | Arg | Glu | Asn | Leu | Ser | Tyr | Gly | |
| | 50 | | | | | 55 | | | | | 60 | | | | | |

| tgc | gtc | ggc | gtc | acc | tgg | atc | aat | tca | ggc | ttc | tac | ccg | acg | aac | aaa | 240 |
|---|---|---|---|---|---|---|---|---|---|---|---|---|---|---|---|---|
| Cys | Val | Gly | Val | Thr | Trp | Ile | Asn | Ser | Gly | Phe | Tyr | Pro | Thr | Asn | Lys | |
| 65 | | | | | 70 | | | | | 75 | | | | | 80 | |

| ttg | gcg | ttc | gcg | ttc | ttc | gac | gag | aac | aag | tac | aag | aac | gat | ctg | aag | 288 |
|---|---|---|---|---|---|---|---|---|---|---|---|---|---|---|---|---|
| Leu | Ala | Phe | Ala | Phe | Phe | Asp | Glu | Asn | Lys | Tyr | Lys | Asn | Asp | Leu | Lys | |
| | | | | 85 | | | | | 90 | | | | | 95 | | |

| aat | acc | agc | ccc | cga | ccc | aat | gaa | acg | cgg | gcg | gag | ttc | gag | ggc | cgc | 336 |
|---|---|---|---|---|---|---|---|---|---|---|---|---|---|---|---|---|
| Asn | Thr | Ser | Pro | Arg | Pro | Asn | Glu | Thr | Arg | Ala | Glu | Phe | Glu | Gly | Arg | |
| | | | 100 | | | | | 105 | | | | | 110 | | | |

| atc | gcc | aag | gcc | agc | ttc | gac | gag | ggg | aag | ggc | ttc | aag | cgg | gcg | cgt | 384 |
|---|---|---|---|---|---|---|---|---|---|---|---|---|---|---|---|---|
| Ile | Ala | Lys | Ala | Ser | Phe | Asp | Glu | Gly | Lys | Gly | Phe | Lys | Arg | Ala | Arg | |
| | | 115 | | | | | 120 | | | | | 125 | | | | |

| gat | gtg | gcc | tcc | atc | atg | aac | aag | gcc | ctg | gag | aac | gcc | ccc | gac | gag | 432 |
|---|---|---|---|---|---|---|---|---|---|---|---|---|---|---|---|---|
| Asp | Val | Ala | Ser | Ile | Met | Asn | Lys | Ala | Leu | Glu | Asn | Ala | Pro | Asp | Glu | |
| | 130 | | | | | 135 | | | | | 140 | | | | | |

| gga | acg | tac | ctc | aag | aac | ctc | aag | acg | gac | ctc | acg | aac | aaa | aat | gat | 480 |
|---|---|---|---|---|---|---|---|---|---|---|---|---|---|---|---|---|
| Gly | Thr | Tyr | Leu | Lys | Asn | Leu | Lys | Thr | Asp | Leu | Thr | Asn | Lys | Asn | Asp | |
| 145 | | | | | 150 | | | | | 155 | | | | | 160 | |

| gcc | ctg | ctc | cac | gag | gac | agc | cgc | tcg | aac | ttc | tac | tcg | gca | ctg | agg | 528 |
|---|---|---|---|---|---|---|---|---|---|---|---|---|---|---|---|---|
| Ala | Leu | Leu | His | Glu | Asp | Ser | Arg | Ser | Asn | Phe | Tyr | Ser | Ala | Leu | Arg | |
| | | | | 165 | | | | | 170 | | | | | 175 | | |

| aat | aca | ccg | tcc | ttc | agg | gaa | aga | gac | gga | ggc | aac | tac | gac | ccg | tcc | 576 |
|---|---|---|---|---|---|---|---|---|---|---|---|---|---|---|---|---|
| Asn | Thr | Pro | Ser | Phe | Arg | Glu | Arg | Asp | Gly | Gly | Asn | Tyr | Asp | Pro | Ser | |
| | | | 180 | | | | | 185 | | | | | 190 | | | |

| aag | atg | aag | gcg | gtg | atc | tac | tcc | aag | cac | ttc | tgg | agc | ggg | cag | gac | 624 |
|---|---|---|---|---|---|---|---|---|---|---|---|---|---|---|---|---|
| Lys | Met | Lys | Ala | Val | Ile | Tyr | Ser | Lys | His | Phe | Trp | Ser | Gly | Gln | Asp | |
| | | 195 | | | | | 200 | | | | | 205 | | | | |

| cag | cgg | ggc | tcc | gcc | gac | aag | aga | aag | tac | ggc | gac | gcg | gaa | gct | ttc | 672 |
|---|---|---|---|---|---|---|---|---|---|---|---|---|---|---|---|---|
| Gln | Arg | Gly | Ser | Ala | Asp | Lys | Arg | Lys | Tyr | Gly | Asp | Ala | Glu | Ala | Phe | |
| | 210 | | | | | 215 | | | | | 220 | | | | | |

| cgc | ccc | gac | cag | ggc | acc | ggc | ctg | gtc | gac | atg | tcg | aag | gac | aga | aac | 720 |
|---|---|---|---|---|---|---|---|---|---|---|---|---|---|---|---|---|
| Arg | Pro | Asp | Gln | Gly | Thr | Gly | Leu | Val | Asp | Met | Ser | Lys | Asp | Arg | Asn | |
| 225 | | | | | 230 | | | | | 235 | | | | | 240 | |

| att | ccg | cgc | agt | ccg | gcc | cgt | cct | ggc | gaa | ggt | tgg | gtc | aat | ttc | gac | 768 |
|---|---|---|---|---|---|---|---|---|---|---|---|---|---|---|---|---|
| Ile | Pro | Arg | Ser | Pro | Ala | Arg | Pro | Gly | Glu | Gly | Trp | Val | Asn | Phe | Asp | |
| | | | | 245 | | | | | 250 | | | | | 255 | | |

| tac | ggg | tgg | ttc | ggg | gct | caa | acg | gca | gcg | gac | gcc | gac | gaa | aca | aca | 816 |
|---|---|---|---|---|---|---|---|---|---|---|---|---|---|---|---|---|
| Tyr | Gly | Trp | Phe | Gly | Ala | Gln | Thr | Ala | Ala | Asp | Ala | Asp | Glu | Thr | Thr | |
| | | | 260 | | | | | 265 | | | | | 270 | | | |

| tgg | acc | cac | ggc | gac | cac | tat | cac | gca | ccc | aat | agc | ggc | ctg | ggc | ccc | 864 |
|---|---|---|---|---|---|---|---|---|---|---|---|---|---|---|---|---|
| Trp | Thr | His | Gly | Asp | His | Tyr | His | Ala | Pro | Asn | Ser | Gly | Leu | Gly | Pro | |
| | | 275 | | | | | 280 | | | | | 285 | | | | |

| atg | cat | gtc | cac | gag | agc | aag | ttc | cgg | aag | tgg | tcc | gcc | ggg | tac | gcg | 912 |
|---|---|---|---|---|---|---|---|---|---|---|---|---|---|---|---|---|
| Met | His | Val | His | Glu | Ser | Lys | Phe | Arg | Lys | Trp | Ser | Ala | Gly | Tyr | Ala | |
| | 290 | | | | | 295 | | | | | 300 | | | | | |

```
gac ttc gac cgc gga acc tac gtg atc acg ttt ata ccc aag agc tgg      960
Asp Phe Asp Arg Gly Thr Tyr Val Ile Thr Phe Ile Pro Lys Ser Trp
305                 310                 315                 320 aac acc gcc ccc gac aag gtg gag caa ggc tgg ccg                      996
Asn Thr Ala Pro Asp Lys Val Glu Gln Gly Trp Pro
                325                 330

<210> SEQ ID NO 6
<211> LENGTH: 332
<212> TYPE: PRT
<213> ORGANISM: Streptomyces fradiae

<400> SEQUENCE: 6

Ala Leu Val Asp Asp Arg Glu Thr Pro Pro Ala Glu Pro Leu Asp Arg
1               5                   10                  15

Met Pro Asp Ala Tyr Arg Ala Tyr Gly Gly Arg Ala Thr Thr Val Val
                20                  25                  30

Asn Asn Tyr Ile Arg Lys Trp Gln Gln Val Tyr Ser Gln Arg Asp Gly
            35                  40                  45

Lys Lys Gln Gln Met Thr Glu Glu Gln Arg Glu Asn Leu Ser Tyr Gly
    50                  55                  60

Cys Val Gly Val Thr Trp Ile Asn Ser Gly Phe Tyr Pro Thr Asn Lys
65                  70                  75                  80

Leu Ala Phe Ala Phe Phe Asp Glu Asn Lys Tyr Lys Asn Asp Leu Lys
                85                  90                  95

Asn Thr Ser Pro Arg Pro Asn Glu Thr Arg Ala Glu Phe Glu Gly Arg
            100                 105                 110

Ile Ala Lys Ala Ser Phe Asp Glu Gly Lys Gly Phe Lys Arg Ala Arg
        115                 120                 125

Asp Val Ala Ser Ile Met Asn Lys Ala Leu Glu Asn Ala Pro Asp Glu
    130                 135                 140

Gly Thr Tyr Leu Lys Asn Leu Lys Thr Asp Leu Thr Asn Lys Asn Asp
145                 150                 155                 160

Ala Leu Leu His Glu Asp Ser Arg Ser Asn Phe Tyr Ser Ala Leu Arg
                165                 170                 175

Asn Thr Pro Ser Phe Arg Glu Arg Asp Gly Gly Asn Tyr Asp Pro Ser
            180                 185                 190

Lys Met Lys Ala Val Ile Tyr Ser Lys His Phe Trp Ser Gly Gln Asp
        195                 200                 205

Gln Arg Gly Ser Ala Asp Lys Arg Lys Tyr Gly Asp Ala Glu Ala Phe
    210                 215                 220

Arg Pro Asp Gln Gly Thr Gly Leu Val Asp Met Ser Lys Asp Arg Asn
225                 230                 235                 240

Ile Pro Arg Ser Pro Ala Arg Pro Gly Glu Gly Trp Val Asn Phe Asp
                245                 250                 255

Tyr Gly Trp Phe Gly Ala Gln Thr Ala Ala Asp Ala Asp Glu Thr Thr
            260                 265                 270

Trp Thr His Gly Asp His Tyr His Ala Pro Asn Ser Gly Leu Gly Pro
        275                 280                 285

Met His Val His Glu Ser Lys Phe Arg Lys Trp Ser Ala Gly Tyr Ala
    290                 295                 300

Asp Phe Asp Arg Gly Thr Tyr Val Ile Thr Phe Ile Pro Lys Ser Trp
305                 310                 315                 320

Asn Thr Ala Pro Asp Lys Val Glu Gln Gly Trp Pro
                325                 330
```

<210> SEQ ID NO 7
<211> LENGTH: 993
<212> TYPE: DNA
<213> ORGANISM: Streptomyces ladakanum
<220> FEATURE:
<221> NAME/KEY: CDS
<222> LOCATION: (1)..(993)

<400> SEQUENCE: 7

| | | | | | | | | | | | | | | | | |
|---|---|---|---|---|---|---|---|---|---|---|---|---|---|---|---|---|
| gac | tcc | gac | gag | cgg | gtg | act | cct | ccc | gcc | gag | ccg | ctc | gac | cgg | atg | 48 |
| Asp | Ser | Asp | Glu | Arg | Val | Thr | Pro | Pro | Ala | Glu | Pro | Leu | Asp | Arg | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccc | gac | ccg | tac | cgg | ccc | tcg | tac | ggc | agg | gcc | gag | acg | atc | gtc | aac | 96 |
| Pro | Asp | Pro | Tyr | Arg | Pro | Ser | Tyr | Gly | Arg | Ala | Glu | Thr | Ile | Val | Asn | |
| | | | 20 | | | | | 25 | | | | | 30 | | | |

| | | | | | | | | | | | | | | | | |
|---|---|---|---|---|---|---|---|---|---|---|---|---|---|---|---|---|
| aac | tac | ata | cgc | aag | tgg | cag | cag | gtc | tac | agc | cac | cgc | gac | ggc | agg | 144 |
| Asn | Tyr | Ile | Arg | Lys | Trp | Gln | Gln | Val | Tyr | Ser | His | Arg | Asp | Gly | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| aaa | cag | cag | atg | acc | gag | gaa | cag | cgg | gag | tgg | ctg | tcc | tac | ggt | tgc | 192 |
| Lys | Gln | Gln | Met | Thr | Glu | Glu | Gln | Arg | Glu | Trp | Leu | Ser | Tyr | Gly | Cys | |
| 50 | | | | | 55 | | | | | 60 | | | | | | |

| | | | | | | | | | | | | | | | | |
|---|---|---|---|---|---|---|---|---|---|---|---|---|---|---|---|---|
| gtc | ggt | gtc | acc | tgg | gtc | aac | tcg | ggc | cag | tat | ccg | acg | aac | agg | ctg | 240 |
| Val | Gly | Val | Thr | Trp | Val | Asn | Ser | Gly | Gln | Tyr | Pro | Thr | Asn | Arg | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gct | ttc | gcg | ttc | ttc | gac | gag | gac | aag | tac | aag | aac | gag | ctg | aag | aac | 288 |
| Ala | Phe | Ala | Phe | Phe | Asp | Glu | Asp | Lys | Tyr | Lys | Asn | Glu | Leu | Lys | Asn | |
| | | | | 85 | | | | | 90 | | | | | 95 | | |

| | | | | | | | | | | | | | | | | |
|---|---|---|---|---|---|---|---|---|---|---|---|---|---|---|---|---|
| ggc | agg | ccc | cgg | tcc | ggc | gaa | acg | cgg | gcg | gag | ttc | gag | ggg | cgc | gtc | 336 |
| Gly | Arg | Pro | Arg | Ser | Gly | Glu | Thr | Arg | Ala | Glu | Phe | Glu | Gly | Arg | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| gcc | aag | gac | agc | ttc | gac | gag | gcg | aag | ggg | ttc | cag | cgg | gcg | cgt | gac | 384 |
| Ala | Lys | Asp | Ser | Phe | Asp | Glu | Ala | Lys | Gly | Phe | Gln | Arg | Ala | Arg | Asp | |
| | | | 115 | | | | | 120 | | | | | 125 | | | |

| | | | | | | | | | | | | | | | | |
|---|---|---|---|---|---|---|---|---|---|---|---|---|---|---|---|---|
| gtg | gcg | tcc | gtc | atg | aac | aag | gcc | ctg | gag | aac | gcc | cac | gac | gag | ggg | 432 |
| Val | Ala | Ser | Val | Met | Asn | Lys | Ala | Leu | Glu | Asn | Ala | His | Asp | Glu | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| gcg | tac | ctc | gac | aac | ctc | aag | aag | gag | ctg | gcg | aac | ggc | aac | gac | gcc | 480 |
| Ala | Tyr | Leu | Asp | Asn | Leu | Lys | Lys | Glu | Leu | Ala | Asn | Gly | Asn | Asp | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctg | cgg | aac | gag | gat | gcc | cgc | tcg | ccc | ttc | tac | tcg | gcg | ctg | cgg | aac | 528 |
| Leu | Arg | Asn | Glu | Asp | Ala | Arg | Ser | Pro | Phe | Tyr | Ser | Ala | Leu | Arg | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| acg | ccg | tcc | ttc | aag | gac | cgc | aac | ggc | ggc | aat | cac | gac | ccg | tcc | aag | 576 |
| Thr | Pro | Ser | Phe | Lys | Asp | Arg | Asn | Gly | Gly | Asn | His | Asp | Pro | Ser | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| atg | aag | gcc | gtc | atc | tac | tcg | aag | cac | ttc | tgg | agc | ggc | cag | gac | cgg | 624 |
| Met | Lys | Ala | Val | Ile | Tyr | Ser | Lys | His | Phe | Trp | Ser | Gly | Gln | Asp | Arg | |
| | | | 195 | | | | | 200 | | | | | 205 | | | |

| | | | | | | | | | | | | | | | | |
|---|---|---|---|---|---|---|---|---|---|---|---|---|---|---|---|---|
| tcg | ggc | tcc | tcc | gac | aag | agg | aag | tac | ggc | gac | ccg | gag | gcc | ttc | cgc | 672 |
| Ser | Gly | Ser | Ser | Asp | Lys | Arg | Lys | Tyr | Gly | Asp | Pro | Glu | Ala | Phe | Arg | |
| | 210 | | | | | 215 | | | | | 220 | | | | | |

| | | | | | | | | | | | | | | | | |
|---|---|---|---|---|---|---|---|---|---|---|---|---|---|---|---|---|
| ccc | gac | cgc | ggc | acc | ggc | ctg | gtc | gac | atg | tcg | agg | gac | agg | aac | att | 720 |
| Pro | Asp | Arg | Gly | Thr | Gly | Leu | Val | Asp | Met | Ser | Arg | Asp | Arg | Asn | Ile | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ccg | cgc | agc | ccc | acc | agc | ccc | ggc | gag | agt | ttc | gtc | aat | ttc | gac | tac | 768 |
| Pro | Arg | Ser | Pro | Thr | Ser | Pro | Gly | Glu | Ser | Phe | Val | Asn | Phe | Asp | Tyr | |
| | | | | 245 | | | | | 250 | | | | | 255 | | |

| | | | | | | | | | | | | | | | | |
|---|---|---|---|---|---|---|---|---|---|---|---|---|---|---|---|---|
| ggc | tgg | ttc | gga | gcg | cag | acg | gaa | gcg | gac | gcc | gac | aag | acc | gta | tgg | 816 |
| Gly | Trp | Phe | Gly | Ala | Gln | Thr | Glu | Ala | Asp | Ala | Asp | Lys | Thr | Val | Trp | |
| | | | 260 | | | | | 265 | | | | | 270 | | | |

```
acc cac ggc aac cac tac cac gcg ccc aat ggc agc ctg ggt gcc atg       864
Thr His Gly Asn His Tyr His Ala Pro Asn Gly Ser Leu Gly Ala Met
        275                 280                 285 cac gtg tac gag agc aag ttc cgc aac tgg tcc gac ggt tac tcg gac       912
His Val Tyr Glu Ser Lys Phe Arg Asn Trp Ser Asp Gly Tyr Ser Asp
    290                 295                 300 ttc gac cgc gga gcc tac gtg gtc acg ttc gtc ccc aag agc tgg aac       960
Phe Asp Arg Gly Ala Tyr Val Val Thr Phe Val Pro Lys Ser Trp Asn
305                 310                 315                 320 acc gcc ccc gac aag gtg aca cag ggc tgg ccg                           993
Thr Ala Pro Asp Lys Val Thr Gln Gly Trp Pro
                325                 330

<210> SEQ ID NO 8
<211> LENGTH: 331
<212> TYPE: PRT
<213> ORGANISM: Streptomyces ladakanum

<400> SEQUENCE: 8

Asp Ser Asp Glu Arg Val Thr Pro Pro Ala Glu Pro Leu Asp Arg Met
1               5                   10                  15

Pro Asp Pro Tyr Arg Pro Ser Tyr Gly Arg Ala Glu Thr Ile Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Phe Phe Asp Glu Asp Lys Tyr Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Asp Ser Phe Asp Glu Ala Lys Gly Phe Gln Arg Ala Arg Asp
        115                 120                 125

Val Ala Ser Val Met Asn Lys Ala Leu Glu Asn Ala His Asp Glu Gly
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Asp Arg Asn Gly Asn His Asp Pro Ser Lys
            180                 185                 190

Met Lys Ala Val Ile Tyr Ser Lys His Phe Trp Ser Gly Gln Asp Arg
        195                 200                 205

Ser Gly Ser Ser Asp Lys Arg Lys Tyr Gly Asp Pro Glu Ala Phe Arg
    210                 215                 220

Pro Asp Arg Gly Thr Gly Leu Val Asp Met Ser Arg Asp Arg Asn Ile
225                 230                 235                 240

Pro Arg Ser Pro Thr Ser Pro Gly Glu Ser Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285
```

```
His Val Tyr Glu Ser Lys Phe Arg Asn Trp Ser Asp Gly Tyr Ser Asp
    290                 295                 300

Phe Asp Arg Gly Ala Tyr Val Val Thr Phe Val Pro Lys Ser Trp Asn
305                 310                 315                 320

Thr Ala Pro Asp Lys Val Thr Gln Gly Trp Pro
                325                 330

<210> SEQ ID NO 9
<211> LENGTH: 993
<212> TYPE: DNA
<213> ORGANISM: Streptomyces lydicus
<220> FEATURE:
<221> NAME/KEY: CDS
<222> LOCATION: (1)..(993)

<400> SEQUENCE: 9 gca gcc gac gaa agg gtc acc cct ccc gcc gag ccg ctc aac cgg atg      48
Ala Ala Asp Glu Arg Val Thr Pro Pro Ala Glu Pro Leu Asn Arg Met
1               5                   10                  15 cct gac gcg tac cgg gcc tac gga ggt agg gcc act acg gtc gtc aac      96
Pro Asp Ala Tyr Arg Ala Tyr Gly Gly Arg Ala Thr Thr Val Val Asn
                20                  25                  30 aac tac ata cgc aag tgg cag cag gtc tac agt cac cgc gac ggc atc     144
Asn Tyr Ile Arg Lys Trp Gln Gln Val Tyr Ser His Arg Asp Gly Ile
            35                  40                  45 caa cag caa atg acc gaa gag cag cga gaa aag ctg tcc tac ggc tgc     192
Gln Gln Gln Met Thr Glu Glu Gln Arg Glu Lys Leu Ser Tyr Gly Cys
        50                  55                  60 gtc ggc atc acc tgg gtc aat tcg ggc ccc tac ccg acg aat aaa ttg     240
Val Gly Ile Thr Trp Val Asn Ser Gly Pro Tyr Pro Thr Asn Lys Leu
65                  70                  75                  80 gcg ttc gcg ttc ttc gac gag aac aag tac aag agt gac ctg gaa aac     288
Ala Phe Ala Phe Phe Asp Glu Asn Lys Tyr Lys Ser Asp Leu Glu Asn
                85                  90                  95 agc agg cca cgc ccc aat gag acg caa gcc gag ttt gag ggg cgc atc     336
Ser Arg Pro Arg Pro Asn Glu Thr Gln Ala Glu Phe Glu Gly Arg Ile
            100                 105                 110 gtc aag gac agt ttc gac gag ggg aag ggt ttc aag cgg gcg cgt gat     384
Val Lys Asp Ser Phe Asp Glu Gly Lys Gly Phe Lys Arg Ala Arg Asp
        115                 120                 125 gtg gcg tcc gtc atg aac aag gcc ctg gat agt gcg cac gac gag ggg     432
Val Ala Ser Val Met Asn Lys Ala Leu Asp Ser Ala His Asp Glu Gly
    130                 135                 140 act tac atc gac aac ctc aag acg gag ctc gcg aac aaa aat gac gct     480
Thr Tyr Ile Asp Asn Leu Lys Thr Glu Leu Ala Asn Lys Asn Asp Ala
145                 150                 155                 160 ctg cgc tac gag gac ggt cgc tcg aac ttt tac tcg gcg ctg agg aat     528
Leu Arg Tyr Glu Asp Gly Arg Ser Asn Phe Tyr Ser Ala Leu Arg Asn
                165                 170                 175 acg ccg tcc ttc aag gaa agg gat gga ggt aac tac gac cca tcc aag     576
Thr Pro Ser Phe Lys Glu Arg Asp Gly Gly Asn Tyr Asp Pro Ser Lys
            180                 185                 190 atg aag gcg gtg gtc tac tcg aaa cac ttc tgg agc ggg cag gac cag     624
Met Lys Ala Val Val Tyr Ser Lys His Phe Trp Ser Gly Gln Asp Gln
        195                 200                 205 cgg ggc tcc tct gac aag agg aag tac ggc gac ccg gat gcc ttc cgc     672
Arg Gly Ser Ser Asp Lys Arg Lys Tyr Gly Asp Pro Asp Ala Phe Arg
    210                 215                 220 ccc gac cag ggc aca ggc ctg gta gac atg tcg aag gac agg aat att     720
Pro Asp Gln Gly Thr Gly Leu Val Asp Met Ser Lys Asp Arg Asn Ile
225                 230                 235                 240
```

```
ccg cgc agt ccc gcc caa cct ggc gaa agt tgg gtc aat ttc gac tac     768
Pro Arg Ser Pro Ala Gln Pro Gly Glu Ser Trp Val Asn Phe Asp Tyr
            245                 250                 255 ggc tgg ttt ggg gct cag acg gaa tcg gac gcc gac aaa acc ata tgg     816
Gly Trp Phe Gly Ala Gln Thr Glu Ser Asp Ala Asp Lys Thr Ile Trp
        260                 265                 270 acc cac gcc aac cac tat cac gcg ccc aac ggc ggc ctg ggc ccc atg     864
Thr His Ala Asn His Tyr His Ala Pro Asn Gly Gly Leu Gly Pro Met
        275                 280                 285 aac gta tat gag agc aag ttc cgg aac tgg tct gcc ggg tac gcg gat     912
Asn Val Tyr Glu Ser Lys Phe Arg Asn Trp Ser Ala Gly Tyr Ala Asp
    290                 295                 300 ttc gac cgc gga acc tac gtc atc acg ttc ata ccc aag agc tgg aac     960
Phe Asp Arg Gly Thr Tyr Val Ile Thr Phe Ile Pro Lys Ser Trp Asn
305                 310                 315                 320 acc gcc ccc gcc gag gta aag cag ggc tgg tcg                         993
Thr Ala Pro Ala Glu Val Lys Gln Gly Trp Ser
                325                 330

<210> SEQ ID NO 10
<211> LENGTH: 331
<212> TYPE: PRT
<213> ORGANISM: Streptomyces lydicus

<400> SEQUENCE: 10

Ala Ala Asp Glu Arg Val Thr Pro Pro Ala Glu Pro Leu Asn Arg Met
1               5                   10                  15

Pro Asp Ala Tyr Arg Ala Tyr Gly Gly Arg Ala Thr Thr Val Val Asn
            20                  25                  30

Asn Tyr Ile Arg Lys Trp Gln Gln Val Tyr Ser His Arg Asp Gly Ile
        35                  40                  45

Gln Gln Gln Met Thr Glu Gln Arg Glu Lys Leu Ser Tyr Gly Cys
    50                  55                  60

Val Gly Ile Thr Trp Val Asn Ser Gly Pro Tyr Pro Thr Asn Lys Leu
65                  70                  75                  80

Ala Phe Ala Phe Phe Asp Glu Asn Lys Tyr Lys Ser Asp Leu Glu Asn
                85                  90                  95

Ser Arg Pro Arg Pro Asn Glu Thr Gln Ala Glu Phe Glu Gly Arg Ile
            100                 105                 110

Val Lys Asp Ser Phe Asp Glu Gly Lys Gly Phe Lys Arg Ala Arg Asp
        115                 120                 125

Val Ala Ser Val Met Asn Lys Ala Leu Asp Ser Ala His Asp Glu Gly
    130                 135                 140

Thr Tyr Ile Asp Asn Leu Lys Thr Glu Leu Ala Asn Lys Asn Asp Ala
145                 150                 155                 160

Leu Arg Tyr Glu Asp Gly Arg Ser Asn Phe Tyr Ser Ala Leu Arg Asn
                165                 170                 175

Thr Pro Ser Phe Lys Glu Arg Asp Gly Asn Tyr Asp Pro Ser Lys
            180                 185                 190

Met Lys Ala Val Val Tyr Ser Lys His Phe Trp Ser Gly Gln Asp Gln
        195                 200                 205

Arg Gly Ser Ser Asp Lys Arg Lys Tyr Gly Asp Pro Asp Ala Phe Arg
    210                 215                 220

Pro Asp Gln Gly Thr Gly Leu Val Asp Met Ser Lys Asp Arg Asn Ile
225                 230                 235                 240

Pro Arg Ser Pro Ala Gln Pro Gly Glu Ser Trp Val Asn Phe Asp Tyr
```

-continued

```
                     245                 250                 255
Gly Trp Phe Gly Ala Gln Thr Glu Ser Asp Ala Asp Lys Thr Ile Trp
            260                 265                 270

Thr His Ala Asn His Tyr His Ala Pro Asn Gly Gly Leu Gly Pro Met
        275                 280                 285

Asn Val Tyr Glu Ser Lys Phe Arg Asn Trp Ser Ala Gly Tyr Ala Asp
    290                 295                 300

Phe Asp Arg Gly Thr Tyr Val Ile Thr Phe Ile Pro Lys Ser Trp Asn
305                 310                 315                 320

Thr Ala Pro Ala Glu Val Lys Gln Gly Trp Ser
                325                 330

<210> SEQ ID NO 11
<211> LENGTH: 996
<212> TYPE: DNA
<213> ORGANISM: Streptomyces platensis
<220> FEATURE:
<221> NAME/KEY: CDS
<222> LOCATION: (1)..(996)

<400> SEQUENCE: 11 gac gcc gtc gat gac agg gtg acc cct ccc gcc gag ccg ctc aac cgg      48
Asp Ala Val Asp Asp Arg Val Thr Pro Pro Ala Glu Pro Leu Asn Arg
1               5                   10                  15 atg cct gac gcg tac cgg gcc tac gga ggc agg gcc act acg gtc gtc      96
Met Pro Asp Ala Tyr Arg Ala Tyr Gly Gly Arg Ala Thr Thr Val Val
            20                  25                  30 aac aac tac ata cgc aag tgg cag cag gtc tac agt caa cgc ggc ggc     144
Asn Asn Tyr Ile Arg Lys Trp Gln Gln Val Tyr Ser Gln Arg Gly Gly
        35                  40                  45 aac cca cag caa atg acc gaa gag cag cga gaa caa ctg tcc tac ggc     192
Asn Pro Gln Gln Met Thr Glu Glu Gln Arg Glu Gln Leu Ser Tyr Gly
    50                  55                  60 tgc gtc ggc gtc acc tgg gtc aat aca ggc ccc tac ccg acg aac aaa     240
Cys Val Gly Val Thr Trp Val Asn Thr Gly Pro Tyr Pro Thr Asn Lys
65                  70                  75                  80 ctc gcg ttc gcg ttc ttc gac gag aac aag tac aag aac gac ctg gaa     288
Leu Ala Phe Ala Phe Phe Asp Glu Asn Lys Tyr Lys Asn Asp Leu Glu
                85                  90                  95 aac agc aga ccg cga ccc aac gag acg cag gcg gag ttc gag ggg cgc     336
Asn Ser Arg Pro Arg Pro Asn Glu Thr Gln Ala Glu Phe Glu Gly Arg
            100                 105                 110 atc gcc aag gac agt ttc gat gag gga aag ggt ttc aag cgg gcg cgt     384
Ile Ala Lys Asp Ser Phe Asp Glu Gly Lys Gly Phe Lys Arg Ala Arg
        115                 120                 125 gag gtg gca tcc gtc atg aac aag gcc ctg gat aac gcg cac gac gag     432
Glu Val Ala Ser Val Met Asn Lys Ala Leu Asp Asn Ala His Asp Glu
    130                 135                 140 gag act tac atc ggc cac ctc aag aca gag ctc gcg aac aaa aac gac     480
Glu Thr Tyr Ile Gly His Leu Lys Thr Glu Leu Ala Asn Lys Asn Asp
145                 150                 155                 160 gct ctg ctc tac gag gac agc cgc tcg agc ttt tac tcg gcg ctg agg     528
Ala Leu Leu Tyr Glu Asp Ser Arg Ser Ser Phe Tyr Ser Ala Leu Arg
                165                 170                 175 aat acg ccg tcc ttc aag gaa agg gat gga ggc aac tac gac ccg tcc     576
Asn Thr Pro Ser Phe Lys Glu Arg Asp Gly Gly Asn Tyr Asp Pro Ser
            180                 185                 190 aag atg aag gcg gtg gtc tac tcg aag cac ttc tgg agc ggg cag gac     624
Lys Met Lys Ala Val Val Tyr Ser Lys His Phe Trp Ser Gly Gln Asp
        195                 200                 205
```

```
cag cgg ggc tcc tcc gag aag agg aag tac ggt gac ccg gac gcc ttc      672
Gln Arg Gly Ser Ser Glu Lys Arg Lys Tyr Gly Asp Pro Asp Ala Phe
    210                 215                 220 cgc ccc ggc cag ggc aca ggt ctg gta gac atg tcg agg gac agg aac      720
Arg Pro Gly Gln Gly Thr Gly Leu Val Asp Met Ser Arg Asp Arg Asn
225                 230                 235                 240 att ccg cgt agt ccc gca aaa cct ggc gaa agt tgg gtc aat ttc gac      768
Ile Pro Arg Ser Pro Ala Lys Pro Gly Glu Ser Trp Val Asn Phe Asp
                245                 250                 255 tac ggc tgg ttc ggg gct cag gca gaa gcg gat gcc gac aaa acc gta      816
Tyr Gly Trp Phe Gly Ala Gln Ala Glu Ala Asp Ala Asp Lys Thr Val
            260                 265                 270 tgg acc cac gcc aac cac tat cat gcg ccc aat ggc ggc atg ggc ccc      864
Trp Thr His Ala Asn His Tyr His Ala Pro Asn Gly Gly Met Gly Pro
        275                 280                 285 atg aac gta tac gag agc aag ttc cgg aac tgg tct gcg ggg tac gcg      912
Met Asn Val Tyr Glu Ser Lys Phe Arg Asn Trp Ser Ala Gly Tyr Ala
    290                 295                 300 gac ttc gac cgc gga gcc tac gtc atc acg ttc ata ccc aag agc tgg      960
Asp Phe Asp Arg Gly Ala Tyr Val Ile Thr Phe Ile Pro Lys Ser Trp
305                 310                 315                 320 aac acc gcc ccc gcc gag gtg aag cag ggc tgg ccg                      996
Asn Thr Ala Pro Ala Glu Val Lys Gln Gly Trp Pro
                325                 330
```

<210> SEQ ID NO 12
<211> LENGTH: 332
<212> TYPE: PRT
<213> ORGANISM: Streptomyces platensis

<400> SEQUENCE: 12

```
Asp Ala Val Asp Asp Arg Val Thr Pro Pro Ala Glu Pro Leu Asn Arg
1               5                   10                  15

Met Pro Asp Ala Tyr Arg Ala Tyr Gly Gly Arg Ala Thr Thr Val Val
            20                  25                  30

Asn Asn Tyr Ile Arg Lys Trp Gln Gln Val Tyr Ser Gln Arg Gly Gly
        35                  40                  45

Asn Pro Gln Gln Met Thr Glu Glu Gln Arg Glu Gln Leu Ser Tyr Gly
    50                  55                  60

Cys Val Gly Val Thr Trp Val Asn Thr Gly Pro Tyr Pro Thr Asn Lys
65                  70                  75                  80

Leu Ala Phe Ala Phe Phe Asp Glu Asn Lys Tyr Lys Asn Asp Leu Glu
                85                  90                  95

Asn Ser Arg Pro Arg Pro Asn Glu Thr Gln Ala Glu Phe Glu Gly Arg
            100                 105                 110

Ile Ala Lys Asp Ser Phe Asp Glu Gly Lys Gly Phe Lys Arg Ala Arg
        115                 120                 125

Glu Val Ala Ser Val Met Asn Lys Ala Leu Asp Asn Ala His Asp Glu
    130                 135                 140

Glu Thr Tyr Ile Gly His Leu Lys Thr Glu Leu Ala Asn Lys Asn Asp
145                 150                 155                 160

Ala Leu Leu Tyr Glu Asp Ser Arg Ser Phe Tyr Ser Ala Leu Arg
                165                 170                 175

Asn Thr Pro Ser Phe Lys Glu Arg Asp Gly Gly Asn Tyr Asp Pro Ser
            180                 185                 190

Lys Met Lys Ala Val Val Tyr Ser Lys His Phe Trp Ser Gly Gln Asp
        195                 200                 205
```

Gln Arg Gly Ser Ser Glu Lys Arg Lys Tyr Gly Asp Pro Asp Ala Phe
            210                 215                 220

Arg Pro Gly Gln Gly Thr Gly Leu Val Asp Met Ser Arg Asp Arg Asn
225                 230                 235                 240

Ile Pro Arg Ser Pro Ala Lys Pro Gly Glu Ser Trp Val Asn Phe Asp
                245                 250                 255

Tyr Gly Trp Phe Gly Ala Gln Ala Glu Ala Asp Ala Asp Lys Thr Val
            260                 265                 270

Trp Thr His Ala Asn His Tyr His Ala Pro Asn Gly Gly Met Gly Pro
            275                 280                 285

Met Asn Val Tyr Glu Ser Lys Phe Arg Asn Trp Ser Ala Gly Tyr Ala
    290                 295                 300

Asp Phe Asp Arg Gly Ala Tyr Val Ile Thr Phe Ile Pro Lys Ser Trp
305                 310                 315                 320

Asn Thr Ala Pro Ala Glu Val Lys Gln Gly Trp Pro
                325                 330

<210> SEQ ID NO 13
<211> LENGTH: 26
<212> TYPE: DNA
<213> ORGANISM: Artificial Sequence
<220> FEATURE:
<223> OTHER INFORMATION: PCR primer

<400> SEQUENCE: 13
aaattcctgt gaattagctg atttag                                          26

<210> SEQ ID NO 14
<211> LENGTH: 39
<212> TYPE: DNA
<213> ORGANISM: Artificial Sequence
<220> FEATURE:
<223> OTHER INFORMATION: PCR primer

<400> SEQUENCE: 14 cttccccgc gccattgtcc gcagtcgcac gtcgcggcg                              39

<210> SEQ ID NO 15
<211> LENGTH: 19
<212> TYPE: DNA
<213> ORGANISM: Artificial Sequence
<220> FEATURE:
<223> OTHER INFORMATION: PCR primer

<400> SEQUENCE: 15
gacaatggcg cgggggaag                                                   19

<210> SEQ ID NO 16
<211> LENGTH: 28
<212> TYPE: DNA
<213> ORGANISM: Artificial Sequence
<220> FEATURE:
<223> OTHER INFORMATION: PCR primer

<400> SEQUENCE: 16
cgctcacatc acggccagcc ctgcttta                                         28

TRANSGLUTAMINASE HAVING DISULFIDE BOND INTRODUCED THEREIN

This application is a continuation under 35 U.S.C. §120 of PCT Patent Application No. PCT/JP2008/052470, filed Feb. 14, 2008, which claims priority under 35 U.S.C. §119 to Japanese Patent Application No. 2007-034916, filed on Feb. 15, 2007, which are incorporated in their entireties by reference. The Sequence Listing in electronic format filed herewith is also hereby incorporated by reference in its entirety (File Name: US-406_Seq_List; File Size: 47 KB; Date Created: Aug. 14, 2009.

BACKGROUND OF THE INVENTION

1. Field of the Invention

The present invention relates to mutant proteins of transglutaminase of actinomycetous origin. Transglutaminase (also simply referred to as TG) is widely utilized for food processing and the like since it forms a cross-linking bond between proteins and produces a gel-like substance. Mutant TG with improved thermal and pH stability allows for improved storage stability of TG, reactions at high temperature, expansion of applicable reaction pH range, and the like, making it possible to apply this enzyme to new fields.

2. Brief Description of the Related Art

Transglutaminase is an enzyme that catalyzes the acyl transfer reaction of the γ-carboxamide group in a peptide chain of a protein. When this enzyme acts on a protein, reactions which result in the formation of ε-(γ-Glu)-Lys cross-linking and replacement of Gln with Glu by deamidation can occur. Transglutaminases of animal origin and those of microbial origin are known. The TG enzymes of animal origin are $Ca^{2+}$-dependent, and are distributed in animal organs, skin, blood, and the like. For example, guinea pig liver transglutaminase (K. Ikura et al., Biochemistry, 27, 2898, 1988), human epidermal keratinocyte transglutaminase (M. A. Phillips et al., Proc. Natl. Acad. Sci. U.S.A, 87, 9333, 1990), human blood coagulation factor XIII (A. Ichinose et al., Biochemistry, 25, 6900, 1986), and the like exist. The TG enzymes of microbial origin are $Ca^{2+}$-independent, and have been discovered in the genus *Streptomyces*, for example, *Streptomyces griseocarneus* NBRC 12776, *Streptomyces cinnamoneus* NBRC 12852, *Streptomyces mobaraensis* NBRC 13819, and the like. A transglutaminase found in a culture supernatant of a variant of *Streptomyces mobaraensis* is referred to as MTG (Microbial Transglutaminase). Furthermore, a $Ca^{2+}$-independent transglutaminase has also been discovered in *Streptomyces lydicus* NRRL B-3446 (JP-A-10-504721). It has been found, as a result of peptide mapping and gene structural analysis, that the primary structures of the transglutaminases produced by these microorganisms do not have any homology with those of animal origin (EP 0 481 504 A1).

MTG is a monomeric protein consisting of 331 amino acids, and having a molecular weight of about 38,000 (T. Kanaji et al., Journal of Biological Chemistry. 268, 11565, 1993). Because MTG is produced from a culture of one of the aforementioned microorganisms, and the like, through a purifying operation, there have been problems with respect to obtaining sufficient yields, efficiency, and the like. Attempts have also been made to produce transglutaminase by genetic engineering techniques. A method based on secretory expression by *Escherichia coli* (*E. coli*), yeast, and the like (JP-A-5-199883), a method wherein *Escherichia coli* is allowed to express MTG as a protein inclusion body, after which this inclusion body is solubilized with a protein denaturant, treated to remove the denaturant, and then reconstituted to produce active MTG (JP-A-6-30771), and a method for secretory expression of MTG using *Corynebacterium glutamicum* (WO2002/081694) have been reported. Unlike transglutaminases of animal origin, MTG and other transglutaminases of microbial origin are $Ca^{24}$-independent, and are hence utilized for production of gelled foods such as jellies, yoghurt, cheese, or gel cosmetics, and the like, as well as improvement of the quality of meat, and the like (JP-A-64-27471). MTG is also utilized for production of raw materials for heat-stable microcapsules, carriers for immobilized enzymes and the like, and is therefore a highly useful industrial enzyme. Regarding enzymatic reaction conditions, a gelled food, for example, does not set if the enzymatic reaction time is too short, and conversely, if the reaction time is too long, the gelled food becomes too hard to be a commercial product. Hence, when MTG is utilized for production of gelled foods such as jellies, yoghurt, cheese, or gel cosmetics and the like, as well as improvement of the quality of meat and the like, the desired product is prepared by adjusting substrate and enzyme concentrations, reaction temperature, and reaction time. However, as MTG-based foods, reagents and the like have become increasingly diverse, there have been some cases where the desired product cannot be prepared solely by adjusting concentrations, temperature, time and the like. Therefore, there is a need for modifying the enzymatic activity of MTG.

Wild-type MTG (wild-type MTG means an MTG that occurs naturally and has not undergone a modification in the amino acid sequence thereof) is known to be stable at a pH between about 4 and 10, and is usually stable over a relatively broad range of pH values, but the reaction of wild-type MTG under extremely acidic or alkaline conditions is difficult. The optimum temperature for reacting wild-type MTG is about 55° C., but such reactions are difficult due to the high temperatures. Even at lower temperatures, incubation for a long time can result in reduced enzymatic activity. Therefore, a mutant transglutaminase with improved pH stability, thermal stability and the like, if any, would enable new uses of transglutaminase.

MTG has been utilized mainly in the food area so far. Feasibility of application in a wide variety of uses, including textiles, chemical products (photographic films, tanning), feeds, cosmetics, and pharmaceuticals, has been suggested.

In the textile area, wool modification with transglutaminase is known. Specifically, it is known that by treating wool with transglutaminase, anti-shrinkage quality, anti-pilling quality and hydrophobicity can be conferred while maintaining the original texture (JP-A-3-213574). When transglutaminase is used for wool, a reaction to keratin at high temperature in a short time, if possible, would increase throughput per unit time and improve production efficiency, and is thought to be industrially useful.

Tanning refers to a process wherein an animal hide/skin is subjected to a series of treatments and steps to render the hide/skin into a durable, flexible leather. This processing is achieved by cross-linking the collagen of the hide/skin with hexavalent chromium. Because hexavalent chromium is harmful and the release thereof into the environment is unwanted, there is a strong demand for the development of an alternative method. Regarding the utilization of transglutaminase for tanning, U.S. Pat. No. 6,849,095 discloses that a transglutaminase of microbial origin can be used for tanning, but discloses no examples of actually allowing the transglutaminase to act on a hide/skin; a transglutaminase has not yet been practically applied for this purpose. Because cross-linking with hexavalent chromium takes place at pH 3 to 4, transglutaminase should also be able to react at this pH, but because MTG is labile to acidity, actual application is difficult.

Hence, when used in applications such as textile processing and tanning, the thermal stability (i.e., heat resistance) of transglutaminase is improved so that the reaction is completed at a high temperature in a short time, and the pH stability is improved so that the reaction can occur under acidic conditions.

As stated above, as a means for modifying and improving the enzymatic activity of transglutaminase, in addition to investigating reaction conditions, modifications of the transglutaminase itself, that is, improvement of the thermal stability and pH stability of the transglutaminase and the like can be mentioned. For example, improving the thermal stability broadens the applicability, which leads to the expectation of increased reaction rates and the like. Also, improving the pH stability will allow the enzymatic reaction to occur under a broader range of pH values, as well as improving the storage stability. This will also be advantageous in industrialization.

To modify the heat resistance and/or pH stability of MTG, it is necessary to prepare a mutant of the MTG, evaluate the activity and the like thereof, and screen for an excellent mutant, that is, a mutant with improved heat resistance and/or pH stability. To prepare a mutant, it is necessary to manipulate the wild-type gene; therefore, a genetically recombinant protein can be prepared. In the case of MTG, a secretory expression system using *Corynebacterium glutamicum* is known (WO2002/081694).

Secretory expression systems of *Corynebacterium* are known as the Sec system and the Tat system. In the Sec system, a protein is secreted prior to formation of a higher structure, whereas the Tat system is characterized in that a protein is secreted through the cell membrane after forming a higher structure in the cell (J. Biol. Chem. 25; 273(52): 34868-74, 1998). The Sec system occurs widely, from prokaryotic organisms such as *Escherichia coli* and *Bacillus subtilis*, to yeast, fungi, and even to eukaryotic organisms such as humans, and is the most important and most general protein secretion pathway. The Tat system also makes it possible to efficiently secrete a heterogeneous protein, which is difficult to secrete with the Sec system (WO2005/103278). Because MTG can be secreted, whether the Sec system or the Tat system is used, secretion with the Tat system can be attempted if a modification has inhibited secretion with the Sec system.

To increase the stability of a protein, it is generally possible to use a method wherein a non-covalent bond, such as a hydrogen bond, an electrostatic interaction, or a hydrophobic interaction, or a covalent bond, such as a disulfide bond, is introduced to enhance the packing of the hydrophobic core in the molecule, or to stabilize the α helix in the secondary structure. Alternatively, another method which can be used to increase the stability of a protein is to remove a factor that makes the structure of the protein unstable. To increase the stability of a protein by introducing a disulfide bond, it is necessary to find a position suitable for introducing cysteine.

SUMMARY OF THE INVENTION

It is an aspect of the present invention to provide a mutant transglutaminase protein which has improved heat resistance and/or pH stability compared with the wild-type (hereinafter "WT") transglutaminase, and to provide a transglutaminase that allows an enzymatic reaction to occur at a high temperature in a short time and/or over a broader range of pH. The mutant transglutaminase is suitable for textile processing, tanning and the like.

It has been found that by introducing a cysteine that allows for the formation of a disulfide bond into a particular position in the amino acid sequence of WT transglutaminase protein, a transglutaminase mutant protein with improved heat resistance and/or pH stability can be produced.

It is an aspect of the present invention to provide a protein possessing transglutaminase activity selected from the group consisting of:

(A) a protein comprising the amino acid sequence of SEQ ID NO: 2, but having a mutation selected from the group consisting of:
  a) substitution of the amino acids at positions 7 and 58 with cysteine,
  b) substitution of the amino acids at positions 46 and 318 with cysteine,
  c) substitution of the amino acids at positions 93 and 112 with cysteine,
  d) substitution of the amino acids at positions 106 and 213 with cysteine,
  e) substitution of the amino acids at positions 160 and 228 with cysteine,
  f) substitution of the amino acids at positions 2 and 282 with cysteine,
  g) substitution of the amino acids at positions 2 and 283 with cysteine,
  h) substitution of the amino acids at positions 3 and 283 with cysteine, and
  i) substitution of the amino acids at positions 17 and 330 with cysteine;

(B) the protein of (A), but also having one or more substitutions, deletions, additions and/or insertions of one or several amino acids in said sequence, and wherein said protein has transglutaminase activity;

(C) the protein of (B), which is at least 70% homologous to the amino acid sequence of SEQ ID NO: 2;

(D) a protein comprising an amino acid sequence selected from the group consisting of SEQ ID NO: 4, 6, 8, 10, and 12, but wherein said sequence has a mutation selected from the group consisting of:
  a) substitution of the amino acids at positions 7 and 58 with cysteine,
  b) substitution of the amino acids at positions 46 and 318 with cysteine,
  c) substitution of the amino acids at positions 93 and 112 with cysteine,
  d) substitution of the amino acids at positions 106 and 213 with cysteine,
  e) substitution of the amino acids at positions 160 and 228 with cysteine,
  f) substitution of the amino acids at positions 2 and 282 with cysteine,
  g) substitution of the amino acids at positions 2 and 283 with cysteine,
  h) substitution of the amino acids at positions 3 and 283 with cysteine, and
  i) substitution of the amino acids at positions 17 and 330 with cysteine;
wherein said positions correspond to those in SEQ ID NO: 2;

(E) the protein of (D), wherein said sequence can also have one or more substitutions, deletions, additions and/or insertions of one or several amino acids in said sequence, and wherein said protein has transglutaminase activity; and (F) the protein of (E), which is at least 70% homologous to an amino acid sequence selected from the group consisting of SEQ ID NO: 4, 6, 8, 10, and 12.

It is a further aspect of the invention to provide a polynucleotide that encodes the protein described above.

It is a further aspect of the invention to provide a recombinant vector comprising the polynucleotide described above.

It is a further aspect of the invention to provide a host cell transformed with the recombinant vector described above.

It is a further aspect of the invention to provide a method of producing a protein, comprising culturing a host cell which has been transformed with a recombinant vector comprising the polynucleotide described above, and collecting a protein possessing transglutaminase activity.

It is a further aspect of the invention to provide a method of processing a substrate protein, comprising a step selected from the group consisting of: (A) allowing the protein described above to act on the substrate protein, (B) allowing a protein produced by culturing a host cell which has been transformed with a recombinant vector comprising the polynucleotide which encodes the protein as described above to act on the substrate protein, and (C) allowing a host cell which has been transformed with a recombinant vector comprising the polynucleotide which encodes the protein as described above to act on the substrate protein.

It is a further aspect of the invention to provide the method described above, wherein the processing of the substrate protein is performed at 40° C. to 100° C.

It is a further aspect of the invention to provide the method described above, wherein the processing of the substrate protein is performed under conditions involving pH 3 to 4.

A transglutaminase with improved heat resistance and/or pH stability obtained by a modification of WT transglutaminase can be provided. Furthermore, by using a transglutaminase with improved heat resistance and/or pH stability, novel products and novel technologies can be provided.

BRIEF DESCRIPTION OF THE DRAWINGS

FIG. 3 shows the residual activity (%) of the T7-E58 (7/58) mutant at various pH levels.

FIG. 4 shows the alignment of the amino acid sequences of MTG and various actinomycete-derived TGs. Conserved amino acid residues are indicated by *.

FIG. 5 shows the residual activity (%) of each mutant after heating at 60° C. for 10 minutes.

FIG. 6 shows the residual activity (%) of each mutant after heating at 60° C. for 10 minutes.

FIG. 7 shows the residual activity (%) of each mutant after retention at pH 3, pH 6, and pH 12 for 1 hour.

DESCRIPTION OF THE PREFERRED EMBODIMENTS

Figures 1, 2:
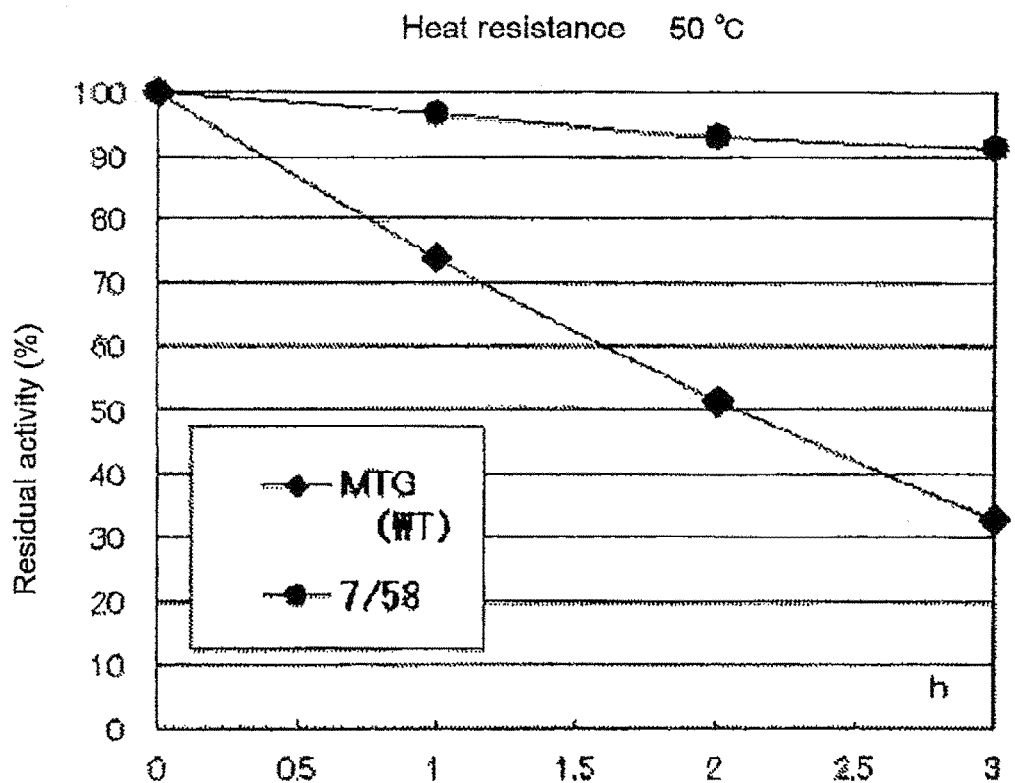
FIG. 1 shows the residual activity (%) of each mutant after heating at the indicated temperatures for 10 minutes.
FIG. 2 shows the residual activity (%) of the T7-E58 (7/58) mutant after heating at 50° C. for 1, 2, and 3 hours.

Transglutaminase is widely utilized for the production of foods such as gelatin, cheese, yoghurt, tofu, kamaboko, hams, sausages, and noodles, as well as for improving the quality of meat, and the like (JP-A-SHO-64-27471). Transglutaminase is also utilized for the production of raw materials for heat-stable microcapsules, carriers for immobilized enzymes and the like, and is used in industry for various purposes. Transglutaminase catalyzes the acyl transfer reaction of the γ-carboxamide group of a glutamine residue in a peptide chain of a protein molecule. When the ε-amino group of a lysine residue in a protein molecule acts as an acyl receptor, an ε-(γ-Glu)-Lys bond is formed in the protein molecule and between the molecules.

Transglutaminases are roughly divided into $Ca^{2+}$-dependent ones, which are of animal origin, and $Ca^{2+}$-independent ones, which are of microbial origin. As TGs of microbial origin, those derived from actinomycetes are known. Representative examples of nucleotide sequences and amino acid sequences of various actinomycete-derived TGs are shown in the table below.

TABLE 1

| Actinomycete | Nucleotide sequence | Amino acid sequence |
| --- | --- | --- |
| Streptomyces mobaraensis | SEQ ID NO: 1 | SEQ ID NO: 2 |
| Streptomyces cinnamoneus | SEQ ID NO: 3 | SEQ ID NO: 4 |
| Streptomyces fradiae | SEQ ID NO: 5 | SEQ ID NO: 6 |
| Streptomyces ladakanum | SEQ ID NO: 7 | SEQ ID NO: 8 |
| Streptomyces lydicus | SEQ ID NO: 9 | SEQ ID NO: 10 |
| Streptomyces platensis | SEQ ID NO: 11 | SEQ ID NO: 12 |

Even when using a transglutaminase homologue other than the above, a mutant protein with improved heat resistance and/or pH stability can be obtained in accordance with the exemplary methods described herein. Specifically, because the amino acid sequences of the transglutaminases can vary slightly depending on the microbial species and strains from which they are derived, the amino acid sequences of transglutaminases that can be modified to obtain exemplary mutant proteins of the present invention are not limited to the amino acid sequences Nos. 2, 4, 6, 8, 10 and 12. That is, any protein possessing transglutaminase activity, and having a homology of 70% or more, in another example 80% or more, in another example 90% or more, in another example 95% or more, and in another example 98% or more, to SEQ ID NOs: 2, 4, 6, 8, 10 or 12, can be used to obtain an exemplary mutant of the present invention. Such a protein can be obtained by aligning the various sequences, identifying corresponding amino acid residues, and introducing a mutation in place of the chosen amino acid residue. As mentioned here, "homology" refers to identity.

For homology analysis, calculations can be made using, for example, the default parameters of "Genetyx ver. 7 (Genetyx Corporation)".

Furthermore, a polynucleotide that hybridizes with a sequence complementary to the nucleotide sequence shown by the aforementioned SEQ ID NOs: 1, 3, 5, 7, 9 or 11, or a probe that can be prepared from these sequences, under stringent conditions, and that encodes a protein possessing transglutaminase activity, can also be used to prepare an exemplary mutant protein of the present invention.

Examples of "stringent conditions" include conditions under which mutually highly homologous nucleotide sequences, for example, nucleotide sequences having a mutual homology of 80, 90, 95, 97 or 99% or more, hybridize to each other, and under which mutually less homologous nucleotide sequences do not hybridize to each other, specifically, ordinary Southern hybridization washing conditions, i.e., conditions involving 1 time, and in another example, 2 to 3 times, of washing at a salt concentration and temperature equivalent to 60° C., 1×SSC, 0.1% SDS, and in another example 0.1×SSC, 0.1% SDS, and in another example 68° C., 0.1×SSC, 0.1% SDS, and the like.

As a probe, a partial sequence of the nucleotide sequence of SEQ ID NOs: 1, 3, 5, 7, 9 or 11 can also be used. Such a probe can be prepared by PCR using an oligonucleotide prepared on the basis of the nucleotide sequence as a primer, and with a DNA fragment which includes the nucleotide sequence of SEQ ID NOs: 1, 3, 5, 7, 9 or 11 as a template. For example, when a DNA fragment about 300 bp long is used as a probe, as hybridization washing conditions, 50° C., 2×SSC, 0.1% SDS can be mentioned.

A transglutaminase can be obtained by, for example, subjecting a product expressed and secreted by a microorganism and the like (including the transformants described below) to the steps of separation, recovery, purification, and the like. A transglutaminase may also be expressed by a microorganism, and the like.

"Transglutaminase activity" means, as stated above, an activity which results in the formation of a cross-linking between a glutamine residue and a lysine residue in a protein. The transglutaminase activity can also be measured after separation and purification from a microorganism and the like, as well when expressed in a microorganism and the like.

Transglutaminase activity can be assayed by the hydroxamate method (J. Biol. Chem., 241, 5518-5525, 1966).

Each activity unit of transglutaminase in the hydroxamate method is defined as follows. Specifically, a reaction is carried out with benzyloxycarbonyl-L-glutaminylglycine and hydroxylamine as substrates, and the resulting hydroxamic acid is converted to an iron complex in the presence of trichloroacetic acid, after which the amount thereof is measured at an absorbance of 525 nm. A working curve is thus generated from the measured values of the amount of hydroxamic acid, and the amount of enzyme that produces 1 μmol of hydroxamate in 1 minute is defined as 1 unit of activity of transglutaminase. Details of this method of measurement have been reported (see, for example, JP-A-SHO-64-27471 and the like).

"WT (wild-type) transglutaminase" means a naturally occurring transglutaminase which does not have a mutation introduced into the amino acid sequence thereof. If the heat resistance and/or pH stability of a transglutaminase mutant protein has "improved" compared with the heat resistance and/or pH stability of WT transglutaminase, this mutant protein is an exemplary mutant of the present invention.

Herein, "an improvement of heat resistance (i.e., thermal stability)" means that the enzyme is able to retain its activity for a longer time, even when subjected to a temperature range that is inappropriate for WT transglutaminase over a long time (for example, about 10 minutes or more), or a temperature at which the activity of WT transglutaminase is considerably reduced by incubation over a long time. For example, at a temperature of about 50° C. or more, in another example about 55° C. or more, in another example about 60° C. or more, in another example about 65° C. or more, and in another example about 68° C. or more, the exemplary mutant enzyme is able to retain its activity for a longer time. Hence, "an improvement of heat resistance" means that when a transglutaminase is incubated at a temperature in this range (for example, about 50° C., about 55° C., about 60° C., about 65° C., about 68° C.) for a long time (for example, about 1 hour, about 2 hours, about 3 hours), the ratio of activity reduction is smaller than that with WT.

An exemplary transglutaminase mutant protein of the present invention is, for example, a protein that has a residual activity of 1% or more, 3% or more, preferably 10% or more, and more preferably 20% or more, after being heated at 65° C. for 10 minutes.

Herein, "an improvement of pH stability" means that the enzyme is able to retain its activity, even within a pH range that is inappropriate for WT transglutaminase, for example, at a pH at which the activity of WT transglutaminase decreases considerably. For example, at an acidic pH of about 4 or less (in one example, a pH of about 3 to 4), or for example, at an alkaline pH of about 10 or more, the mutant exemplary enzyme is able to retain its activity. An exemplary mutant transglutaminase of the present invention is a transglutaminase with improved stability particularly in an acidic zone.

To improve the heat resistance and/or pH stability of MTG, a cysteine residue capable of forming a disulfide bond (SS bond) is introduced into the MTG gene. The site into which the cysteine is introduced is determined as described below. The distance between $C_\beta$ atoms in the steric structure is calculated for pairs of amino acid residues which are separated from each other by 10 residues or more in the primary sequence of the mature region of MTG, and pairs present within a distance of 5 Å, or in another example, 4.5 Å, are extracted. Of these, pairs with side chains of either member which interact with another residue via a hydrogen bond, or forms a hydrophobic core, are excluded because the modification to form an SS bond can affect the essential stability.

After introduction of the mutation, the base sequence is confirmed. Introduction of the mutation can be achieved by various known methods, for example, by using Stratagene QuikChange II Site-Directed Mutagenesis Kit and the like.

An exemplary mutant transglutaminase protein of the present invention is a protein of SEQ ID NO:2, but has one or more of the following a) to i):

a) substitution of the amino acids at positions 7 and 58 with cysteine, b) substitution of the amino acids at positions 46 and 318 with cysteine, c) substitution of the amino acids at positions 93 and 112 with cysteine, d) substitution of the amino acids at positions 106 and 213 with cysteine, e) substitution of the amino acids at positions 160 and 228 with cysteine, f) substitution of the amino acids at positions 2 and 282 with cysteine, g) substitution of the amino acids at positions 2 and 283 with cysteine, h) substitution of the amino acids at positions 3 and 283 with cysteine, i) substitution of the amino acids at positions 17 and 330 with cysteine.

Another example of the mutant transglutaminase protein of the present invention is a protein having the amino acid sequence with the mutations as described above, but in addition to these mutations, may also have substitutions, deletions, additions and/or insertions of one to several residues. Furthermore, another example of the mutant transglutaminase protein of the present invention is a protein having the amino acid sequence which has the mutations (substitution to cysteine) as described above (in at least one position selected from among positions corresponding to a) to i)) in an amino acid sequence selected from among SEQ ID NO:4, 6, 8, 10 and 12. Also, any of the above exemplary proteins may have an amino acid sequence having a homology of 70% or more, in another example, 80% or more, in another example 90% or more, in another example 95% or more, in another example 98% or more to an amino acid sequence selected from among SEQ ID NO:2, 4, 6, 8, 10 and 12, and possessing transglutaminase activity.

The amino acid sequences described above can be an amino acid sequence having, in addition to at least one mutation selected from among a) to i), substitutions, deletions, additions and/or insertions of one to several residues at the respective positions shown in a) to i) and/or other positions.

Herein, positions "corresponding to" the aforementioned positions in an amino acid sequence selected from among SEQ ID NO:4, 6, 8, 10 and 12 are determined by aligning these sequences with the amino acid sequence of SEQ ID NO:2. It is also possible to align the amino acid sequence of a transglutaminase homologue other than any one shown herein with the amino acid sequence of SEQ ID NO:2 to determine "a corresponding" position, and to introduce a mutation into the position. For example, when a gap is introduced into an alignment of SEQ ID NO:2 with another sequence, attention should be paid to the possible forward or backward shift of the position mentioned above. For corresponding positions, see, for example, FIG. 4.

Algorithms used for the alignment of amino acid sequences include NCBI BLAST (National Center for Biotechnology Information Basic Local Alignment Search Tool), the algorithm described in Karlin et al., Proc. Natl. Acad. Sci. USA, 90:5873-5877 (1993) [the algorithm is incorporated in the NBLAST and XBLAST programs (version 2.0) (Altschul et al., Nucleic Acids Res., 25:3389-3402 (1997))], the algorithm described in Needleman et al., J. Mol. Biol., 48:444-453 (1970) [the algorithm is incorporated in the GAP program in the GCG software package], the algorithm described in Myers and Miller, CABIOS, 4:11-17 (1988) [the algorithm is incorporated in the ALIGN program (version 2.0), which is part of the CGC sequence alignment software package], the algorithm described in Pearson et al., Proc. Natl. Acad. Sci. USA, 85:2444-2448 (1988) [the algorithm is incorporated in the FASTA program in the GCG software package] and the like.

Besides the transglutaminase (MTG) derived from *Streptomyces mobaraensis*, an enzyme possessing transglutaminase activity recognized as having some amino acid sequence homology to this enzyme can also be modified, or an enzyme possessing transglutaminase activity which is expected to have a steric structure similar to that of this enzyme, on the basis of the steric structure of MTG. An amino acid substitution that is effective in modifying the substrate specificity and the like in MTG is postulated to also be effective in related enzymes derived from microorganisms such as *Streptomyces cinnamoneus* and *Streptomyces lydicus* (JP-T-HEI-10-504721).

An exemplary mutant protein of the present invention may have a mutation to cysteine described above in only a single pair or in a plurality of pairs, as long as the transglutaminase mutant protein obtained possesses transglutaminase activity, particularly as far as the improved heat resistance and/or pH stability. Such a protein can be prepared by a method publicly known in the art.

The above-described substitutions, deletions, additions and/or insertions are not particularly limited, as long as the transglutaminase mutant protein possesses transglutaminase activity, particularly as far as the improved heat resistance and/or pH stability. Although the number of substitutions, deletions, additions and/or insertions present in such a mutant protein can be one to several residues (1 to 30, in another example 1 to 15, in another example 1 to 5, 3 or 2 residues), an optionally chosen number of amino acid substitutions, insertions, additions and/or deletions may be present, as long as the mutant protein possesses transglutaminase activity, particularly as far as the improved heat resistance and/or pH stability. For example, when this mutation is a substitution, a substitution with a similar amino acid (i.e., conservative amino acid substitution) is assumed to be unlikely to influence the function of the protein, so a substitution with a similar amino acid is preferable. Here, "a similar amino acid" means an amino acid having similar physiochemical properties; examples thereof include amino acids classified under the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr) and amino acids having a small side-chain (Gly, Ala, Ser, Thr, Met). Specific examples of the conservative amino acid substitution are known in the technical field.

A polynucleotide that encodes an exemplary transglutaminase mutant protein of the present invention is also provided. Such a polynucleotide can be acquired using a method known in the art, or, for example, a method described herein. This polynucleotide can be inserted into a vector using an appropriate restriction enzyme to obtain a recombinant vector.

A recombinant vector for use in an exemplary method of the present invention can be chosen as appropriate according to the intended use (for example, cloning, protein expression), or from among ones suitable for the host cell, preferably a microorganism, into which this vector is to be introduced. When this recombinant vector is an expression vector, the expression vector can include an exemplary polynucleotide of the present invention operably ligated to an appropriate promoter, and can include a transcription termination signal, that is, a terminator region, downstream of the polynucleotide. Furthermore, the recombinant vector can further include a selection marker gene (drug resistance genes, genes that compensate for an auxotrophic mutation and the like) for selecting a transformant. The recombinant vector may also include a sequence that encodes a tag sequence useful for the separation/purification of the protein expressed, and the like. The vector may also be one that will be integrated into the genome of the subject host cell.

The vector can be introduced into a host cell using, for example, a known transformation technology such as the competent cell method, protoplast method, calcium phosphate co-precipitation method, polyethylene glycol method, lithium method, electroporation method, microinjection method, liposome fusion method, or particle gun method.

A host cell can also be transformed with such a recombinant vector (hereinafter, also referred to as an exemplary transformant of the present invention). As host cells, prokaryotic cells such as *Escherichia coli* and actinomycetes and eukaryotic cells such as yeast can be mentioned. If the expression of a protein is desired, the host cell should be suitable for protein production, and capable of expressing an exemplary mutant protein of the present invention in a functional form. An exemplary transformant of the present invention can be obtained using one of the transformation technologies mentioned above. Although any microorganism for which a useful recombinant vector system has been developed can be utilized as a host cell; exemplary host cells include, but are not limited to, *E. coli, Corynebacterium glutamicum,* yeast, bacteria of the genus *Bacillus*, various actinomycetes and the like.

An exemplary transformant of the present invention can be cultured under conditions commonly known in the art. For example, culturing temperature, time, medium composition, pH, stirring conditions and the like can be selected as appropriate according to the chosen transformant.

An exemplary transglutaminase mutant protein of the present invention is expressed by an exemplary transformant of the present invention. A transglutaminase mutant protein may be used after secretion from the transformant or purification from the transformant. The transformant may also be used without purifying the exemplary transglutaminsae.

Separation and purification of the protein can be performed according to a known method.

An exemplary transglutaminase mutant protein of the present invention may be first expressed as a pro-form and then treated with an appropriate protease (e.g., subtilisin) to yield a mature form; alternatively, the pro-form and a protease may be expressed at the same time in the chosen host cell to obtain a mature form.

Cultivation of the transformant, and separation and purification of the transglutaminase mutant protein, can be performed, for example, as described below. A kanamycin-containing CM2G medium is dispensed to test tubes. The transformant is inoculated and pre-cultured at 30° C. for 24 hours. An MM medium containing both kanamycin and $CaCO_3$ is dispensed to Sakaguchi flasks at 50 ml per flask, and the pre-culture broth is passaged over generations and cultured. After the culture broth is centrifuged, the supernatant is filtered, and passed through Sephadex G25(M) to replace the solvent with 20 mM phosphate buffer solution, pH 7.0. Subtilisin is added in an amount 1/100 of transglutaminase, and the reaction is allowed to proceed at 30° C. for 16 hours to activate the transglutaminase. The activated solution is exchanged with an equilibration buffer solution for cation exchange chromatography using Sephadex G25(M). Next, the entire amount is loaded onto a cation exchange column (Resource S 6 ml; manufactured by GE Healthcare Bioscience) fully equilibrated with the same buffer solution. After re-equilibration with the same buffer solution, a protein fraction eluted on a linear concentration gradient of 0→0.5 M NaCl at a NaCl concentration of nearly 200 mM is fractionated with UV absorption at a wavelength of 280 nm as an index. The activities and protein contents of the resulting fractions are measured, and fractions with nearly the same specific activity in the vicinity of the peak top, excluding fractions of low specific activity, are recovered. The recovered fractions are passed through Sephadex G25(M) to replace the solvent with 20 mM phosphate buffer solution, pH 6.0. The samples are diluted to a concentration of about 1 mg/ml with 20 mM phosphate buffer solution, pH 6.0, and stored at −80° C. until use.

A method of processing a substrate protein is also provided using an exemplary transglutaminase mutant protein of the present invention, or a transformant expressing the protein. Proteins capable of being a substrate for transglutaminase include proteins having a glutamine residue and/or lysine residue which is/are accessible to the transglutaminase. This method is applicable to various applications wherein a protein cross-linking reaction is desirably performed in a temperature range and/or pH zone that is inappropriate for use of WT transglutaminase (textile processing, tanning and the like).

For example, an exemplary mutant protein of the present invention can be used in a reaction carried out at about 40° C. to about 100° C., in another example, about 50° C. to about 100° C., in another example about 55° C. to about 100° C., in another example about 60° C. to about 100° C., and yet in another example about 65° C. to about 100° C. In particular, because the high temperature treatment used in textile processing is carried out at a temperature of at least about 65° C., an exemplary mutant protein of the present invention is suitable for use in the textile processing.

An exemplary mutant protein of the present invention can be used in a reaction carried out at a pH of about 4 or less, preferably about 3 to about 4. In tanning, in particular, the enzymatic reaction is typically carried out at a pH of 3 to 4; and therefore, an exemplary mutant protein of the present invention is suitable for use in tanning.

For an exemplary mutant protein of the present invention wherein a mutation allowing for the formation of a disulfide bond has been introduced (a disulfide bond-introduced mutant), introduction of a cysteine residue can be confirmed by performing peptide mapping with lysyl endopeptidase. The peptide mapping can be performed with reference to a method described in a reference document (J. Biol. Chem., 268, 16, 11565-11572, 1993). The formation of a disulfide bond can be confirmed by a decrease in the mutant's heat resistance upon reduction with a reducing agent such as dithiothreitol, a change in the molecular weight as detected by MS analysis, and the like.

EXAMPLES

The present invention is hereinafter described more specifically by the following non-limiting examples.

When amino acids and the like are denoted with codes in the description and drawings, the codes are based on the codes specified by the IUPAC-IUB Commission on Biochemical Nomenclature or the common codes in the art.

Example 1

Preparation of Mutant Proteins of MTG with an Incorporated Disulfide (SS) Bond

MTG has no SS bonds. Hence, an SS bond was introduced into MTG, and it was examined whether or not the heat resistance was improved. The site into which an SS bond should be introduced was determined as follows. The distance was calculated between the $C_\beta$ atoms for pairs of amino acid residues which are separated from each other by 10 residues or more in the primary sequence of the mature region of MTG. Pairs present within a distance of 4.5 Å were extracted. Of these, pairs with side chains of either member which interact with another residue via a hydrogen bond, or forms a hydrophobic core, were excluded because the modification to form an SS bond can affect the essential stability. Of these, six pairs estimated to be capable of forming an SS bond were selected. The six pairs are divided into two sets of three pairs. Specifically, the three pairs D46-S318, E93-V112, and A106-D213 have a relatively high value of temperature factor ($C_\beta$ atomic value of about 40 $Å^2$ or more). The three pairs T7-E58, A140-P190, and A160-G228 do not have a particularly high temperature factor, and are present relatively outwardly of the molecule. Regarding the method of mutagenesis, two sites in the mature region of MTG were substituted with Cys.

Regarding the method of substitution, the mutation was introduced into the pro-TG expression plasmid pPSPTG11 (App. Env. Micro., 2003, 69, 3011-3014) using the Stratagene QuikChange II Site-Directed Mutagenesis Kit according to the procedures recommended by the manufacturer. Whether or not the mutation had been introduced was determined by performing a base sequence analysis using the ABI PRISM Cycle Sequencing Kit according to the procedures recommended by the manufacturer. The plasmid incorporating the desired mutation was introduced into a *corynebacterium* (*Corynebacterium glutamicum*) by electroporation. The electroporation was performed by the method described in a reference document (FEMS Microbiol. Lett., 53, 299-303, 1989). A CM2G medium containing 25 μg/ml kanamycin was dispensed into test tubes at 3 ml per tube. The mutant strain was inoculated and pre-cultured at 30° C. for 24 hours. An MM medium containing 25 μg/ml kanamycin, 5 mM DTT, and 50 g/L $CaCO_3$ was dispensed to Sakaguchi flasks at 50 ml per flask, and 2.5 ml of the pre-culture broth was inoculated and cultured at 30° C. for 48 hours. In the mutants of the A140-P190 and A160-G228 pairs, only a trace amount of TG was secreted. The culture broth of each of the remaining four pairs which secreted TG was centrifuged (10,000 rpm, 10 minutes), after which the supernatant was filtered, and passed through Sephadex G25(M) to replace the solvent with 20 mM phosphate buffer solution, pH 7.0. Subtilisin was added in an amount 1/100 of MTG, and the reaction was allowed to proceed at 30° C. for 16 hours to activate the MTG. The activated solution was exchanged with an equilibration buffer solution for cation exchange chromatography (20 mM sodium acetate buffer solution, pH 5.5) using Sephadex G25(M). Next, the entire amount was loaded on a cation exchange column (Resource S 6 ml; manufactured by GE Healthcare Bioscience) fully equilibrated with the same buffer solution. After re-equilibration with the same buffer solution, a protein fraction eluted on a linear concentration gradient of 0→0.5 M NaCl at an NaCl concentration of nearly 200 mM was fractionated with UV absorption at a wavelength of 280 nm as an index. The activities and protein contents of the resulting fractions were measured, and fractions with nearly the same specific activity in the vicinity of the peak top, excluding fractions of low specific activity, were recovered. The activities and protein contents were measured by methods described in a reference document (Prot. Exp. Puri., 2002, 26, 329-335). The recovered fractions were passed through Sephadex G25(M) to replace the solvent with 20 mM phosphate buffer solution, pH 6.0. Chromatography was always performed at room temperature. The samples obtained were diluted to a concentration of about 1 mg/ml with 20 mM phosphate buffer solution, pH 6.0, and stored at −80° C. until use.

For the A140-P190 and A160-G228 mutants, which secreted trace amounts of TG, secretion with the Tat system was attempted. Specifically, with the protein glutaminase secretory expression plasmid pPKT-PPG (WO2005/103278) using the TorA signal as a template, and with the primers having the sequences shown by SEQ ID NO:13 (5'-AAAT-TCCTGTGAATTAGCTGATTTAG-3') and SEQ ID NO:14 (5'-CTTCCCCCGCGCCATTGTCCGCAGTCG-CACGTCGCGGCG-3'), a region including the TorA signal sequence and the CspB promoter upstream of the 5' thereof was amplified. The sequence shown by SEQ ID NO:14 includes a gene sequence that encodes the C-terminal side of the TorA signal sequence and a sequence that encodes the N-terminal side of the pro-sequence of MTG. Also, with the aforementioned pro-TG expression plasmid pPSPTG11 as a template, and using primers of the sequences shown by SEQ ID NO:15 (5'-GACAATGGCGCGGGGGAAG-3') and SEQ ID NO:16 (5'-CGCTCACATCACGGCCAGCCCT-GCTTTA-3'), PCR was performed to amplify the gene sequence that encodes pro-TG. A PCR product amplified with the primers of the sequences shown by SEQ ID NO:13 and SEQ ID NO:14 and a PCR product amplified with the primers of the sequences shown by SEQ ID NO:15 and SEQ ID NO:16 were mixed in a 1:1 ratio; with this mixture as a template, and by means of the primers of the sequences shown by SEQ ID NO:13 and SEQ ID NO:16, a cross-over PCR was performed, to amplify a fusion gene of the CspB promoter, the TorA signal, and the gene that encodes pro-MTG. This PCR product was cleaved using ScaI and EcoO65I, and an about 700 bp gene fragment was recovered by agarose gel electrophoresis. This recovered DNA fragment was inserted into the ScaI-EcoO65I region of pPKSPTG1 (described in WO01/23591) to prepare the pro-TG expression plasmid pPKT-PTG11. The base sequence was determined by the method described above, and it was confirmed that the fusion gene was constructed as expected.

By substituting two sites in the mature region of MTG expressed by means of the pro-TG expression plasmid pPKT-PTG11 with Cys, the A140-P190 mutant and the A160-G228 mutant were prepared. The method of substitution was in accordance with the method described above. A plasmid incorporating the desired mutation was introduced into *Corynebacterium glutamicum* by electroporation. The Tat secretion apparatus expression plasmid pVtatABC was introduced into this strain by electroporation. The electroporation was performed by the method described above. A CM2G medium containing 25 μg/ml kanamycin and 5 μg/ml chloramphenicol was dispensed to test tubes at 3 ml per tube. The mutant strain was inoculated and pre-cultured at 30° C. for 24 hours. An MM medium containing 25 μg/ml kanamycin, 5 μg/ml chloramphenicol and 50 g/L CaCO$_3$ was dispensed to Sakaguchi flasks at 50 ml per flask, 2.5 ml of the pre-culture broth was inoculated and cultured at 30° C. for 48 hours. Purification from the culture broth supernatant was performed by activation with subtilisin and cation exchange chromatography according the method described above. The obtained mutant was treated to replace the solvent with 20 mM phosphate buffer solution, pH 6.0, and stored at −80° C. until use.

Example 2

Evaluation of Heat Resistance of Mutants which have an Incorporated Disulfide (SS) Bond Heat resistance was evaluated on the basis of residual activity after heating. After D46-S318 (46/318), E93-V112 (93/112), A106-D213 (106/213), and T7-E58 (7/58) were adjusted to a concentration of 0.5 mg/ml, each was heated at 55° C., 60° C., 65° C. and 68° C. for 10 minutes, after which their heat resistance was evaluated on the basis of residual activity (%). All these mutants retained some activity even after being heated at 65° C. and 68° C., whereas the wild-type MTG lost activity (FIG. 1). For the T7-E58 (7/58) mutant, heating at 50° C. for 1, 2, and 3 hours was followed by an evaluation of its residual activity by the hydroxamate method; as shown in FIG. 2, a major improvement in the heat resistance was observed. Furthermore, after A140-P190 (140/190) and A160-G228 (160/228) were adjusted to a concentration of 0.1 mg/ml, each was heated at 60° C. for 10 minutes, after which their heat resistance was evaluated on the basis of residual activity (%). Only A160-G228 exhibited improved heat resistance (FIG. 5).

Example 3

Preparation of Mutant Proteins of MTG Incorporating a Disulfide (SS) Bond

Since the heat resistance of the T7-E58 (7/58) mutant improved remarkably in Example 2, introduction of a disulfide bond was further investigated. The site into which an SS bond should be introduced was determined as follows. The distance was calculated between the C$_\beta$ atoms for pairs of amino acid residues which are separated from each other by 10 residues or more in the primary sequence of the mature region of MTG. Pairs present within a distance of 5.0 Å were extracted. Of these, pairs with side chains of either member which interacts with another residue via a hydrogen bond, or forms a hydrophobic core, were excluded because the mutations to form an SS bond can affect the essential stability. Of these, as residue pairs estimated to be capable of forming an SS bond, four pairs that stabilize the vicinity of the N terminus, that is, S2-N282, S2-G283, D3-G283, and P17-W330, were selected. Regarding the method of mutagenesis, two sites in the mature form region of MTG were substituted with Cys. As for how to prepare a plasmid incorporating a desired mutation, and how to prepare and culture *Corynebacterium glutamicum* retaining the plasmid having the desired mutation, operations were performed in the same manner as Example 1. S2-N282, S2-G283, and D3-G283 were purified from culture supernatants by activation with subtilisin and cation exchange chromatography in the same manner as Example 1. P17-W330, without being subjected to purification by cation exchange chromatography, was passed through Sephadex G25(M) to replace the solvent with 20 mM phosphate buffer solution, pH 6.0, and this was used as the sample.

Example 5

Evaluation of Heat Resistance of Mutants with an Incorporated Disulfide (SS) Bond Heat resistance was evaluated on the basis of residual activity after heating. After S2-N282 (2/282), S2-G283 (2/283), and D3-G283 (3/283) were adjusted to a concentration of 0.1 mg/ml, each was heated at 60° C. for 10 minutes, after which their heat resistance was evaluated on the basis of residual activity (%). All these mutants exhibited significantly improved heat resistance compared with the wild type (FIG. 6). Having not been purified, P17-W330 was adjusted to a concentration of 0.1 mg/ml, then heated at 60° C. for 10 minutes, after which its heat resistance was evaluated on the basis of to which extent the residual activity rose compared with the wild type in (%). Compared with the wild type, the residual activity rose by 16%, confirming an improvement in the heat resistance.

Example 6

Evaluation of pH Stability of Mutants with an Incorporated Disulfide (SS) Bond pH stability was evaluated on the basis of residual activity after retention at a specified pH at 4° C. for 1 hour. Specifically, 2 mg/ml MTG and the T7-E58 (7/58) mutant were diluted 4 fold with specified buffer solutions [0.1 M glycine buffer solution (pH 3, 4, 9 and 10), 20 mM phosphate buffer solution (pH 6)], and maintained at 4° C. for 1 hour, after which each was diluted 5 fold with 20 mM phosphate buffer solution, pH 6, and the activity was measured by the hydroxamate method. The results, with the activity at pH 6 expressed as 100%, are shown in FIG. 3. It was found that in the acidic zone, the T7-E58 mutant had higher pH stability than MTG.

Furthermore, 0.4 mg/ml MTG and T7-E58 (7/58), S2-N282 (2/282), S2-G283 (2/283), and D3-G283 (3/283) were diluted 4 fold with specified buffer solutions (0.1 M glycine buffer solution pH 3, 0.1 M sodium phosphate buffer solution pH 12), and maintained at room temperature for 1 hour, after which each was diluted 2 fold with 0.4 M phosphate buffer solution, pH 6, and the activity was measured by the hydroxamate method. The results, with the activity at pH 6 expressed as 100%, are shown in FIG. 7. In all the mutants, acid resistance at pH 3 increased, and in all mutants but 2/282, alkali resistance at pH 12 improved.

Partial Sequence Listing:
SEQ ID NO: 13: PCR primer
SEQ ID NO: 14: PCR primer
SEQ ID NO: 15: PCR primer
SEQ ID NO: 16: PCR primer

INDUSTRIAL APPLICABILITY

According to the present invention, a mutant transglutaminase protein is provided with improved heat resistance compared with the WT protein, in that the time necessary for the enzymatic reaction is shortened, and large amounts of the enzyme can be treated. A mutant transglutaminase protein is provided with improved pH stability (particularly in acidic pH zone), so as to allow enzyme treatment at high temperature and/or under acidic conditions as required in textile processing, tanning and the like.

While the invention has been described in detail with reference to preferred embodiments thereof, it will be apparent to one skilled in the art that various changes can be made, and equivalents employed, without departing from the scope of the invention. Each of the aforementioned documents is incorporated herein in its entirety.

The invention claimed is:

1. A protein possessing transglutaminase activity selected from the group consisting of:
   (A) a protein comprising the amino acid sequence of SEQ ID NO: 2 or a mutant thereof that is at least 70% homologous to the amino acid sequence of SEQ ID NO: 2, but wherein said protein has a mutation selected from the group consisting of:
   a) substitution of the amino acids at positions 7 and 58 with cysteine,
   b) substitution of the amino acids at positions 46 and 318 with cysteine,
   c) substitution of the amino acids at positions 93 and 112 with cysteine,
   d) substitution of the amino acids at position 106 and 213 with cysteine,
   e) substitution of the amino acids at positions 160 and 228 with cysteine,
   f) substitution of the amino acids at positions 2 and 282 with cysteine,
   g) substitution of the amino acids at positions 2 and 283 with cysteine,
   h) substitution of the amino acids at positions 3 and 283 with cysteine, and
   i) substitution of the amino acids at positions 17 and 330 with cysteine;
   (B) a protein comprising an amino acid sequence selected from the group consisting of SEQ ID NO: 4, 6, 8, 10, and 12, or mutants thereof that are at least 70% homologous to the amino acid sequences of SEQ ID NO: 4, 6, 8, 10, and 12, respectively, wherein said protein has a mutation selected from the group consisting of:
   a) substitution of the amino acids at positions 7 and 58 with cysteine,
   b) substitution of the amino acids at positions 46 and 318 with cysteine,
   c) substitution of the amino acids at positions 93 and 112 with cysteine,
   d) substitution of the amino acids at position 106 and 213 with cysteine,
   e) substitution of the amino acids at positions 160 and 228 with cysteine,
   f) substitution of the amino acids at positions 2 and 282 with cysteine,
   g) substitution of the amino acids at positions 2 and 283 with cysteine,
   h) substitution of the amino acids at positions 3 and 283 with cysteine, and
   i) substitution of the amino acids at positions 17 and 330 with cysteine;
   wherein said positions correspond to those in SEQ ID NO: 2.

2. A polynucleotide that encodes the protein of claim 1.

3. A recombinant vector comprising the polynucleotide of claim 2.

4. A host cell transformed with the recombinant vector of claim 3.

5. A method of producing a protein possessing transglutaminase activity, comprising culturing a host cell which has been transformed with a recombinant vector comprising the polynucleotide of claim 2, and separating the protein from the host cell.

6. A method of processing a substrate protein, comprising a step selected from the group consisting of
   A) allowing the protein of claim 1 to act on the substrate protein resulting in the formation of a cross-linking bond in and between the substrate protein(s),
   B) allowing a protein produced by culturing a host cell which has been transformed with a recombinant vector comprising the polynucleotide which encodes the protein of claim 1 to act on the substrate protein resulting in the formation of a cross-linking bond in and between the substrate protein(s), and
   C) allowing a host cell which has been transformed with a recombinant vector comprising the polynucleotide which encodes the protein of claim 1 to act on the substrate protein resulting in the formation of a cross-linking bond in and between the substrate protein(s).

7. The method of claim 6, wherein the processing of the substrate protein is performed at 40° C. to 100° C.

8. The method of claim 6, wherein the processing of the substrate protein is performed at pH 3 to 4.

* * * * *